US007618980B2

(12) United States Patent
Fevig et al.

(10) Patent No.: US 7,618,980 B2
(45) Date of Patent: *Nov. 17, 2009

(54) PYRROLO(OXO)QUINOLINES AS 5HT LIGANDS

(75) Inventors: John M. Fevig, Doylestown, PA (US); Jianxin Feng, Levittown, PA (US); Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 599 days.

This patent is subject to a terminal disclaimer.

(21) Appl. No.: 11/180,861

(22) Filed: Jul. 13, 2005

(65) Prior Publication Data

US 2006/0014778 A1   Jan. 19, 2006

Related U.S. Application Data

(60) Provisional application No. 60/587,690, filed on Jul. 14, 2004.

(51) Int. Cl.
*A61K 31/437* (2006.01)
*C07D 471/04* (2006.01)
(52) U.S. Cl. ......................................... 514/292; 546/81
(58) Field of Classification Search ........................ None
See application file for complete search history.

(56) References Cited

U.S. PATENT DOCUMENTS

| 4,268,513 | A | 5/1981 | Shapiro |
|---|---|---|---|
| 2003/0187254 | A1 | 10/2003 | Perry et al. |

FOREIGN PATENT DOCUMENTS

| WO | WO 99/09025 | 2/1999 |
|---|---|---|
| WO | WO 03/014121 | 2/2003 |
| WO | WO 2004/065351 | 8/2004 |

OTHER PUBLICATIONS

Dorwald F. A. Side Reactions in Organic Synthesis, 2005, Wiley: VCH, Weinheim p. IX of Preface.*
Caplus English Abstract DN 140:146029 Viranyi Andrea et al, 2003.*
Caplus English Abstract DN 140:146025 Nyerges et al, 2003.*
Caplus English Abstract Achini Roland, DN 96: 104021, 1981, vol. 64, Issue7, pp. 2203-2218. See RN #80897-02-5P.
U.S. Appl. No. 11/180,268, filed Jul. 13, 2005, Fevig et al.
Chojnacka-Wójcik, E. et al., "Involvement of 5-$HT_{2C}$ Receptors in the m-CPP-Induced Antinociception in Mice", Pol. J. Pharmacol., vol. 46, pp. 423-428 (1994).
Cryan, J.F. et al., "Antidepressant-Like Behavioral Effects Mediated by 5-Hydroxytryptamine$_{2C}$ Receptors", The Journal of Pharmacology and Experimental Therapeutics, vol. 295, No. 3, pp. 1120-1126 (2000).
Di Matteo, V. et al., "Role of 5-$HT_{2C}$ receptors in the control of central dopamine function", Trends in Pharmacological Sciences, vol. 22, No. 5, pp. 229-232 (2001).

Grottick, A.J. et al., "Activation of 5-$NT_{2C}$ receptors reduces the locomotor and rewarding effects of nicotine", Psychopharmacology, vol. 157, pp. 292-298 (2001).
Grottick, A.J. et al., "Studies to Investigate the Role of 5-$HT_{2C}$ Receptors on Cocaine- and Food- Maintained Behavior", The Journal of Pharmacology and Experimental Therapeutics, vol. 295, No. 3, pp. 1183-1191 (2000).
Hoffman, B.J. et al., "Distribution of serotonin 5-$HT_{1C}$ receptor mRNA in adult rat brain", FEBS Letters, vol. 247, No. 2, pp. 453-462 (1989).
Hoyer, D. et al., "VII. International Union of Pharmacology Classification of Receptors for 5- Hydroxytryptamine (Serotonin)", Pharmacological Reviews, vol. 46, No. 2, pp. 157-203 (1994).
Jones, K. et al., "Intramolecular Reactions Using Amide Links: Aryl Radical Cyclisation of Silylated Acryloylanilides", Tetrahedron Letters, vol. 35, No. 41, pp. 7673-7676 (1994).
Mazzola-Pomietto, P. et al., "Evidence that m-chlorophenylpiperazine-induced hyperthermia in rats is mediated by stimulation of 5-$HT_{2C}$ receptors", Psychopharmacology, vol. 123, pp. 333-339 (1996).
Millan, M.J. et al., "5-$HT_{2C}$ receptors mediate penile erections in rats: actions of novel and selective agonists and antagonists", European Journal of Pharmacology, vol. 325, pp. 9-12 (1997).
Nonogaki, K. et al., "Leptin-independent hyperphagia and type 2 diabetes in mice with a mutated serotonin 5-$HT_{2C}$ receptor gene", Nature Medicine, vol. 4, No. 10, pp. 1152-1156 (1998).
Nyerges, M. et al., "A Convenient Synthesis of Pyrrolo[3,4-c]quinolines", Heterocyclic Communications, vol. 9, No. 3, pp. 239-242 (2003).
Rittenhouse, P.A. et al., "Evidence that ACTH Secretion Is Regulated by Serotonin$_{2A/2C}$ (5-$HT_{2A/2C}$) Receptors", The Journal of Pharmacology and Experimental Therapeutics, vol. 271, No. 3, pp. 1647-1655 (1994).
Sharpley, A.L. et al., "Slow Wave Sleep in Humans: Role of 5-$HT_{2A}$ and 5-$HT_{2C}$ Receptors", Neuropharmacology, vol. 33, No. 3/4, pp. 467-471 (1994).
Vickers, S.P. et al., "Comparative effects of continuous infusion of mCPP, Ro 60-0175 and d- fenfluramine on food intake, water intake, body weight and locomotor activity in rats", British Journal of Pharmacology, vol. 130, pp. 1305-1314 (2000).
Vickers, S.P. et al., "Evidence that hypophagia induced by d-fenfluramine and d-norfenfluramine in the rat is mediated by 5-$HT_{2C}$ receptors", Neuropharmacology, vol. 41, pp. 200-209 (2001).

(Continued)

*Primary Examiner*—Rita J Desai
(74) *Attorney, Agent, or Firm*—Terence J. Bogie

(57) ABSTRACT

The present application provides pyrrolo(oxo)isoquinolines as modulators of serotonin receptors, pharmaceutical compositions containing such modulators and methods for treating various diseases, conditions and disorders associated with modulation of serotonin receptors such as, for example: metabolic diseases, which includes but is not limited to obesity, diabetes, diabetic complications, atherosclerosis, impared glucose tolerance and dyslipidemia; central nervous system diseases which includes but is not limited to, anxiety, depression, obsessive compulsive disorder, panic disorder, psychosis, schizophrenia, sleep disorder, sexual disorder and social phobias; cephalic pain; migraine; and gastrointestinal disorders using such compounds and compositions.

9 Claims, No Drawings

OTHER PUBLICATIONS

Vickers, S.P. et al., "Reduced satiating effect of *d*-fenfluramine in serotonin 5-HT$_{2C}$ receptor mutant mice", Psychopharmacology, vol. 143, pp. 309-314 (1999).

Virányi, A. et al., "A Convenient Synthesis of Pyrrolo[3,4-*c*]quinolines", Synthesis, No. 17, pp. 2655-2660 (2003).

Roy et al., "Studies on the Reaction of Benzoyl Peroxide with NN-Disubstituted Aromatic Amines and Other Related Compounds. Part IV. A Novel Formation of 1,2,3,4-Tetrahydroquinoline Derivatives", Journal of the Chemical Society, Section C: Organic Chemistry, Chemical Society, Letchworth, GB, Jan. 1, 1969, pp. 1886-1891.

Cappelli et al., "Novel Potent 5-HT3 Receptor Ligands Based on the Pyrrolidone Structure: Synthesis, Biological Evaluation, and Computational Rationalization of the Ligand-Receptor Interaction Modalities", Bioorganic & Medicinal Chemistry, vol. 10, 2002, pp. 779-801.

Achini, "215. Synthesis of Phenyl- and Benzyl-Substituted Pyrrolidones and of a Piperidine by intramolecular C-Alkylation. Synthons for Tricyclic Skeletons", Helvetica Chimica ACTA, vol. 64, No. 7, Jan. 1, 1981 pp. 2203-2218.

* cited by examiner

PYRROLO(OXO)QUINOLINES AS 5HT LIGANDS

RELATED APPLICATIONS

This application claims priority benefit under Title 35 § 119(e) of U.S. Provisional Application No. 60/587,690, filed Jul. 14, 2004, the contents of which are herein incorporated by reference.

BACKGROUND

The neurotransmitter/hormone serotonin (5-hydroxytryptamine, 5-HT) regulates many physiological processes via a group of at least 14 distinct receptors that are organized into 7 subfamilies (Hoyer, D., et al., Pharmacol. Rev., 46, 1994). The $5\text{-HT}_2$ subfamily is composed of the $5\text{-HT}_{2A}$, $5\text{-HT}_{2B}$, and $5\text{-HT}_{2C}$ receptors as determined by gene homology and pharmacological properties. There exists a substantial correlation for the relationship between $5\text{-HT}_2$ receptor modulation and a variety of diseases and therapies. Prior to the early 1990's the $5\text{-HT}_{2C}$ and $5\text{-HT}_{2A}$ receptors were referred to as $5\text{-HT}_{1C}$ and $5\text{-HT}_2$, respectively.

The direct or indirect agonism or antagonism of $5\text{-HT}_2$ receptors, either selectively or non-selectively, has been associated with the treatment of various central nervous system (CNS) disorders including obesity, depression, schizophrenia and bi-polar disorders. In the recent past the contribution of serotonergic activity to the mode of action of anti-obesity drugs has been well documented. Compounds that increase the overall basal tone of serotonin in the CNS have been developed as anorectic drugs. The serotonin releasing agents, such as fenfluramine, function by increasing the amount of serotonin present in the nerve synapse. These breakthrough treatments, however, are not without side effects. Due to the mechanism of action of serotonin releasing agents, they effect the activity of a number of serotonin receptor subtypes in a wide variety of organs including those not associated with the desired mechanism of action. This non-specific modulation of the serotonin family of receptors most likely plays a significant role in the side effect profile. In addition, these compounds or their metabolites often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

The $5\text{-HT}_{2C}$ receptor is a G-protein coupled receptor. It is almost exclusively expressed in the central nervous system including the hypothalamus, hippocampus, amygdala, nucleus of the solitary tract, spinal cord, cortex, olfactory bulb, ventral tegmental area (VTA), nucleus accumbens and choroid plexus (Hoffman, B. and Mezey, E., FEBS Lett., 247, 1989). There is ample evidence to support the role of selective $5\text{-HT}_{2C}$ receptor ligands in a number of disease therapies. $5\text{-HT}_{2C}$ knockout mice develop a late stage obesity syndrome that is not reversed by fenfluramine or other direct acting $5\text{-HT}_{2C}$ agonists such as mCPP (Nonogaki, K., et al., Nature Med., 4, 1998; Vickers, S., et. al., Psychopharmacology, 143, 1999). Administration of selective $5\text{-HT}_{2C}$ agonists to rats causes a reduction in food intake and corresponding reduction in body weight (Vickers, S., et al., Br. J. Pharmacol., 130, 2000) and these responses can be blocked by administration of selective $5\text{-HT}_{2C}$ antagonists (Vicker, S., et al., Neuropharmacol., 41, 2001). $5\text{-HT}_{2C}$ receptor modulation in the hypothalamus can also influence thermoregulation (Mazzola-Pomietto, P., et al., Psychopharmacology, 123, 1996), sleep (Sharpley, A., et al., Neuropharmacology, 33, 1994), sexual behavior and neuroendocrine function (Rittenhouse, P. et al., J. Pharmacol. Exp. Ther., 271, 1994). Activation of $5\text{-HT}_{2C}$ receptors in the VTA modulates the activity of dopaminergic neurons that are involved in aspects of depression (Di Matteo, V. et al., Trends Pharmacol. Sci., 22, 2001) and $5\text{-HT}_{2C}$ receptor agonists such as WAY 161503, RO 60-0175 and RO 60-0332 are active in rodent models of depression (Cryan, J. and Lucki, I., J. Pharmacol. Exp. Ther., 295, 2000). $5\text{-HT}_{2C}$ agonists have been reported to reduce the rewarding effects of nicotine administration in rats (Grottick, A., et al., Psychopharmacology, 157, 2001) and influences rodent responses to cocaine administration (Grottick, A., et al., J. Pharmacol. Exp. Ther., 295, 2000). Modulation of $5\text{-HT}_{2C}$ receptors in the spinal cord can influence pain perception (Chojnacka-Wojcik, E., et al., Pol. J. Pharmacol., 46, 1994). There is also data indicating that the $5\text{-HT}_{2C}$ receptor agonists mCPP and RO 60-0175 mediate penile erections in rats (Millan, M., et al., Eur J. Pharmacol. 325, 1997).

DETAILED DESCRIPTION

The present application describes compounds according to Formula I, pharmaceutical compositions, comprising at least one compound according to Formula I and optionally at least one additional therapeutic agent and methods of treating various diseases, conditions and disorders associated with modulation of serotonin receptors such as, for example: metabolic diseases, which includes but is not limited to obesity, diabetes, diabetic complications, atherosclerosis, impared glucose tolerance and dyslipidemia; central nervous system diseases which includes but is not limited to, anxiety, depression, obsessive compulsive disorder, panic disorder, psychosis, schizophrenia, sleep disorder, sexual disorder and social phobias; cephalic pain; migraine; and gastrointestinal disorders using compounds according to Formula I

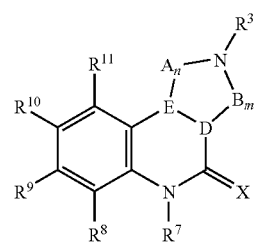

I including all stereoisomers, pharmaceutically acceptable salt forms, solvates and prodrug esters thereof, wherein A, B, D, E, m, n, $R^3$, $R^7$, $R^8$, $R^9$, $R^{10}$, $R^{11}$ and X are described herein, are effective modulators of serotonin receptors.

Definitions

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

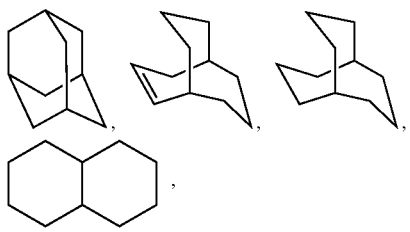

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, alkenyl, alyalkynyl, oxyperfluoroalkyl, oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl, The term "carbo" as used herein as part of another group refers to a carbonyl (C=O) group serving as a linker between two groups such as, for example, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl and thiocycloalkyl.

The term "perfluoro" as used herein as part of another group refers to a group wherein more than one hyrdogen atom attached to one or more carbon atoms in the group has been replaced with a fluorine atom such as, for example, perfluoroalkyl, perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfinyl" as used herein as part of another group refers to an —SO-group such as, for example, sulfinylalkyl, sulfinylalkenyl, sulfinylalkynyl, sulfinylaryl, sulfinylcycloalkyl, sulfinylheterocyclyl and sulfinylheteroaryl.

The term "sulfonyl" as used herein as part of another group refers to an —SO$_2$-group such as, for example, sulfonylalkyl, sulfonylalkenyl, sulfonylalkynyl, sulfonylaryl, sulfonylcycloalkyl, sulfonylheterocyclyl and sulfonylheteroaryl.

An administration of a therapeutic agent of the application includes administration of a therapeutically effective amount of the agent of the application. The term "therapeutically effective amount" as used herein refers to an amount of a therapeutic agent to treat or prevent a condition treatable by administration of a composition of the application. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the application.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:
  a) *The Practice of Medicinal Chemistry*, Camille G. Wermuth et al., Ch 31, (Academic Press, 1996);
  b) *Design of Prodrugs*, edited by H. Bundgaard, (Elsevier, 1985); and
  c) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

All stereoisomers of the compounds of the instant application are contemplated, either in admixture or in pure or substantially pure form. The compounds of the present application can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the application include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

Synthesis

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Scheme 1

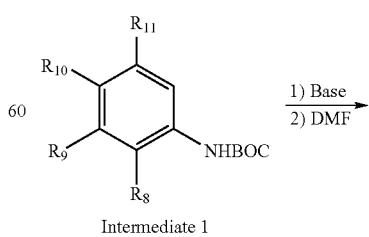

Intermediate 1

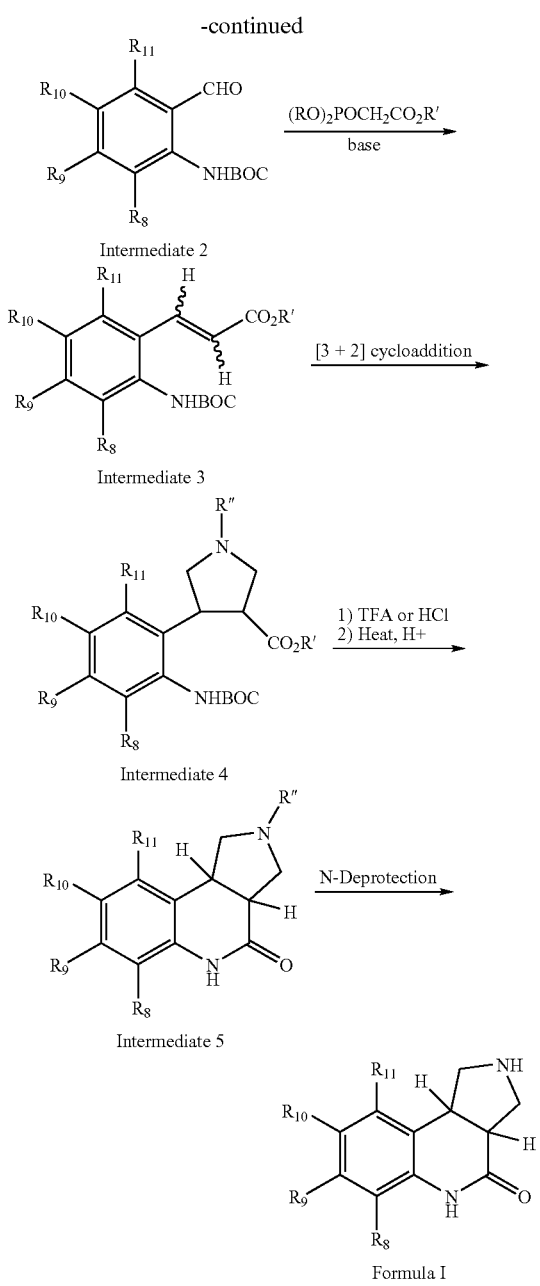

Compounds of Formula I, wherein $A_n$ is $CH_2$ and $B_m$ is $CH_2$, D and E are CH, and X is O, can be prepared as described in Scheme 1. N-Protection of a variety of commercially available or readily prepared anilines with $BOC_2O$ and a base such as triethylamine affords intermediate 1. The carbamate protecting group serves to direct subsequent deprotonation with sec-BuLi (with or without TMEDA, −78° C., THF or ether) to occur at the adjacent aryl-H bond (see Beak, P., et. al., *Tetrahedron Lett.* 1989, 30, 1197; and Iwao, M., et. al., *Heterocycles,* 1992, 34, 1031). Quenching with an appropriate electrophile, such as N,N-dimethylformamide, affords the aldehyde intermediate 2. Horner-Emmons reaction of aldehydes 2 with an appropriate phosphonate reagent in the presence of a base affords the α,β-unsaturated ester intermediate 3, where the olefin geometry can be controlled by the nature of the phosphonate reagent and the conditions of the reaction. For example, under standard conditions, using a phosphonate reagent where R' is Me or Et and using sodium hydride as a base leads to intermediate 3 with the E-olefin geometry as the nearly exclusive product. Alternatively, using a phosphonate reagent where R' is 2,2,2-trifluoroethyl or Ar, generating its potassium enolate with potassium hexamethyldisilazide or potassium carbonate and 18-crown-6, and allowing it to react with aldehyde 2 leads to intermediate 3 with Z-olefin geometry as the nearly exclusive product (see Still, W. C., et. al., *Tetrahedron Lett.* 1983, 24, 4405; for a review of Z-selective Horner-Emmons reactions, see Jiro, M. *Trends Org. Chem.* 1998, 7, 63). Olefin intermediates 3 can serve as dipolarophiles in 1,3-dipolar cycloadditions with appropriate azomethine ylides to afford the pyrrolidine intermediates 4 (for reviews of 1,3-dipolar cycloaddition chemistry of azomethine ylides, see 1,3-*Dipolar Cycloaddition Chemistry*, A. Padwa, Ed., Wiley-Interscience, New York, 1984). The required azomethine ylide can be generated in several ways, two preferred methods of which are described. The commercially available tertiary amine N-(methoxymethyl)-N-(trimethylsilylmethyl)benzylamine can be treated with 5-25 mol % TFA in methylene chloride to generate the required azomethine ylide and 1,3-dipolar cycloaddition then occurs at room temperature or reflux temperature to afford intermediate 4. Alternatively, N-benzylglycine can be refluxed with paraformaldehyde in a suitable solvent such as toluene or benzene to generate the azomethine ylide. These methods produce intermediate 4 where the pyrrolidine nitrogen is protected with a benzyl group. The 1,3-dipolar cycloaddition is stereospecific in that the stereochemistry of the olefin is retained and translated into the relative stereochemistry of the pyrrolidine products. Thus, E-olefins undergo cyclization to produce pyrrolidines 4 with a trans configuration of the 3,4-substituents on the pyrrolidine ring and Z-olefins undergo cyclization to produce pyrrolidines 4 with a cis configuration of the 3,4-substituents on the pyrrolidine ring. Removal of the BOC group under acidic conditions, for example with TFA, affords an aniline which can undergo ring-closing condensation on the ester group, either spontaneously or with heating or with heating in the presence of an acid such as p-toluenesulfonic acid, to afford the intermediate 5. N-Deprotection of intermediate 5 is readily accomplished using a variety of methods found in Greene, T and Wuts, P. G. M., *Protecting Groups in Organic Synthesis*, John Wiley & Sons, Inc., New York, N.Y., 1991, and references therein. For example, when R" in intermediate 5 is N-benzyl, deprotection is achieved by catalytic hydrogenation over Pd/C catalyst or Pd(OH)$_2$/C catalyst, or by reaction with α-chloroethyl chloroformate (ACE-Cl) and subsequent refluxing in methanol. The N-deprotection just described affords compounds of Formula I, wherein $A_n$ is $CH_2$ and $B_m$ is $CH_2$, D and E are CH, and X is O.

Scheme 2

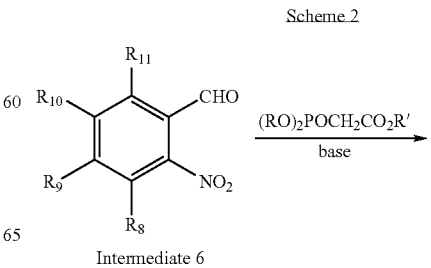

Intermediate 6

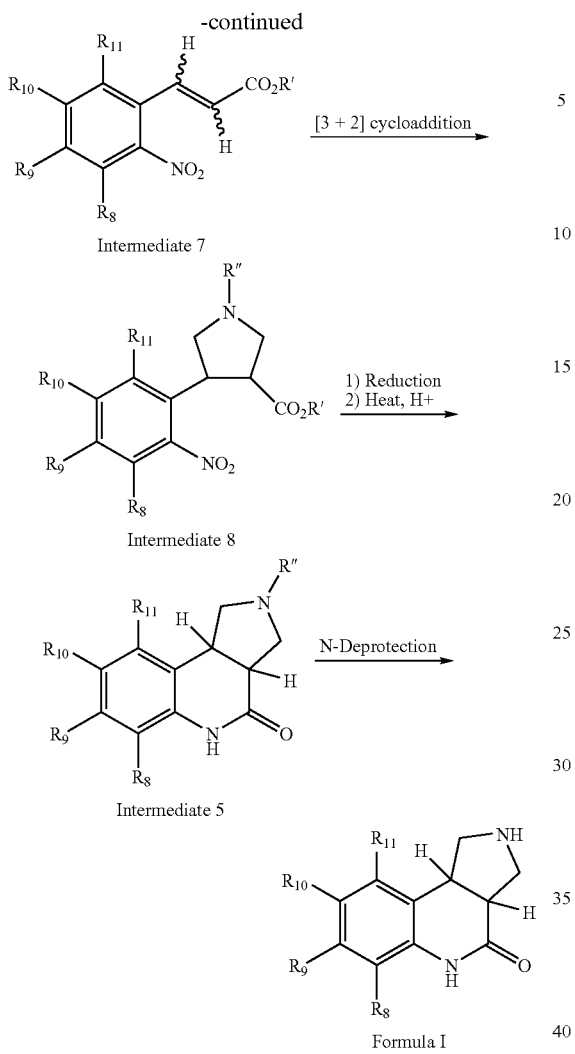

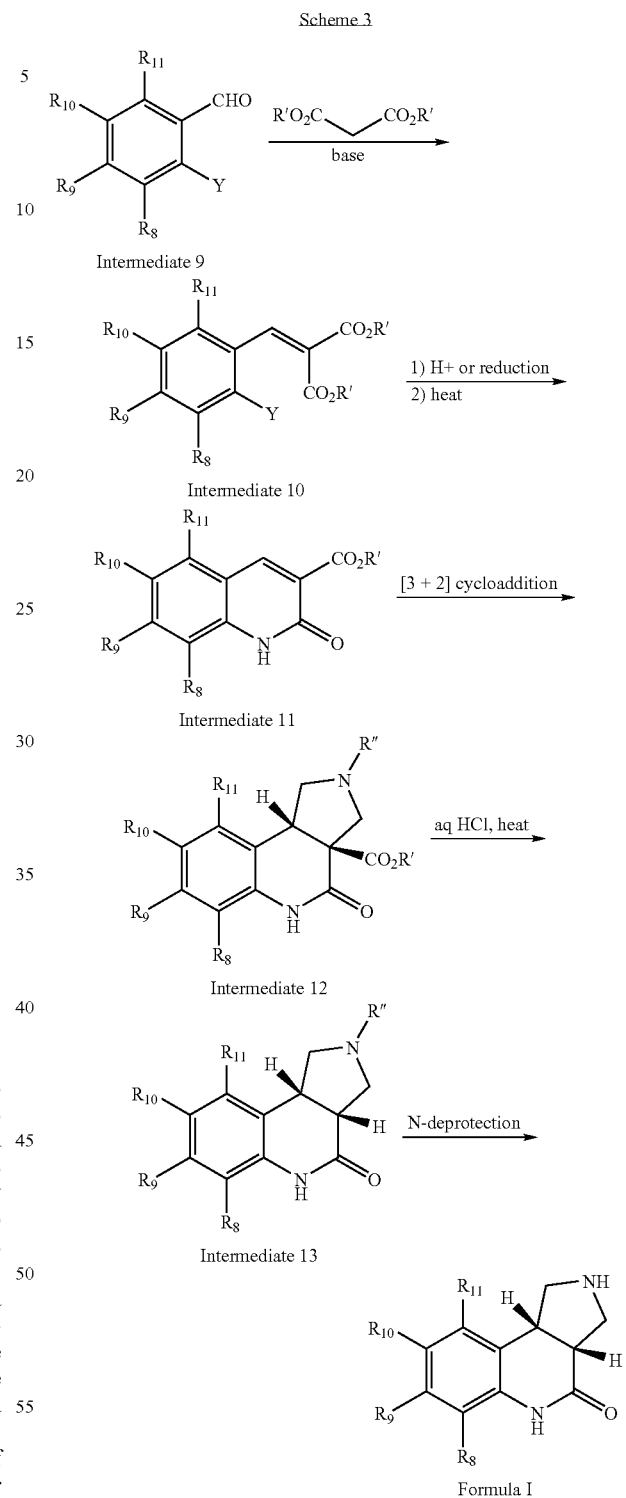

Y = NHBOC or NO₂

Compounds of Formula I, wherein $A_n$ is $CH_2$ and $B_m$ is $CH_2$, D and E are CH, and X is O, can also be prepared as described in Scheme 2. Nitroaldehyde intermediate 6, which are commercially available or can be prepared by methods known to those skilled in the art, can be treated under a variety of Horner-Emmons conditions as described in Scheme 1 to afford intermediate 7 as either the E- or Z-olefin. Also as described in Scheme 1, intermediate 7 can undergo [3+2] cycloaddition with the appropriate azomethine ylide to afford intermediate 8, where the relative stereochemistry of the 3,4-pyrrolidine substituents is dictated by the geometry of the olefin intermediate 7. Reduction of the nitro group can be accomplished by a variety of methods, such as but not limited to treatment with tin(II) chloride in an appropriate solvent, iron in acetic acid, catalytic hydrogenation, etc. The choice of reagent for nitro group reduction will be dictated by other functionality within intermediate 8, as will be recognized by those skilled in the art. Ring closure of the resulting aniline by heating with or without acid, as described in Scheme 1, will afford intermediate 5. N-deprotection of intermediate 5 as described in Scheme 1 or as found in Greene, T and Wuts, P. G. M., *Protecting Groups in Organic Synthesis*, John Wiley & Sons, Inc., New York, N.Y., 1991, will afford compounds of Formula I wherein $A_n$ is $CH_2$ and $B_m$ is $CH_2$, D and E are CH, and X is O.

Alternatively, the compounds of Formula I, wherein $A_n$ is $CH_2$ and $B_m$ is $CH_2$, D and E are CH, X is O, and the ring fusion is cis, can be prepared as described in Scheme 3. The aldehyde intermediate 9, where Y is NHBOC or NO₂, can be prepared as described in Schemes 1 and 2. Condensation of intermediate 9 with dimethyl or diethyl malonate in the presence of catalytic piperidine or piperidine benzoate with removal of water affords an α,β-unsaturated diester intermediate 10. Removal of the BOC group under acidic conditions or reduction of the nitro group as described previously, and subsequent ring-closing condensation, which occurs spontaneously or with heating, affords the intermediate 11. The 1,3-dipolar cycloaddition of this substrate with an appropriately generated azomethine ylide as described in Scheme 1 then affords the intermediate 12 with a cis ring fusion. Alternatively, the order of the previous two operations can be reversed. For example, the [3+2] azomethine ylide cycloaddition can be performed on intermediate 10, affording a pyrrolidine diester intermediate. N-deprotection (where Y=NHBOC) or reduction (where Y=$NO_2$) of this intermediate followed by ring-closing condensation, which occurs spontaneously or with heating, also affords the intermediate 12. Decarboxylation of intermediate 12 can be accomplished by basic hydrolysis followed by heating the resulting acid, such as by refluxing in dioxane, or by heating the intermediate 12 under acidic conditions, to afford intermediate 13, which has retained the cis ring fusion. Intermediates 13 can be converted to the compounds of Formula I, wherein $A_n$ is $CH_2$ and $B_m$ is $CH_2$, D and E are CH, X is O, and the ring fusion is cis, by the procedures described in Scheme 1.

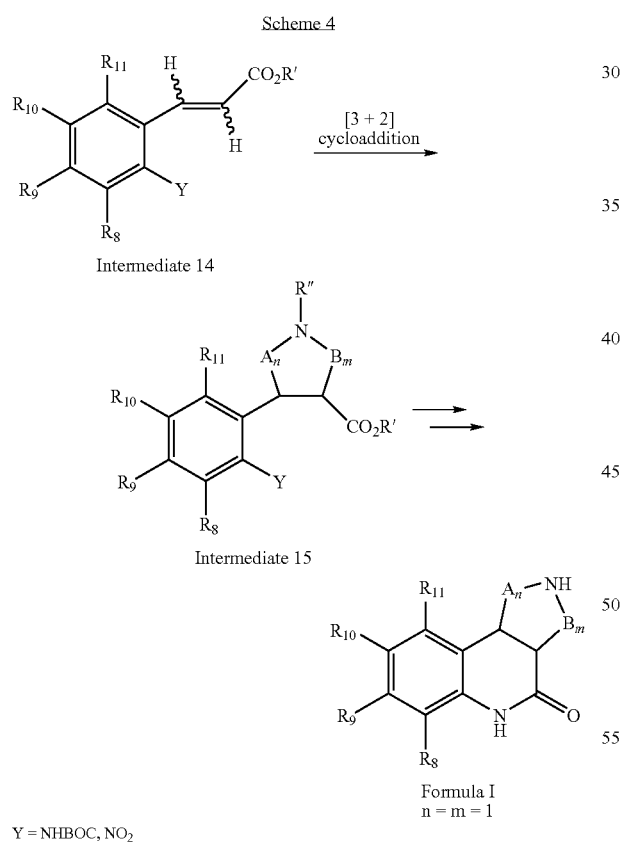

Y = NHBOC, $NO_2$

It is well known to those skilled in the art that a variety of additional methods can be used to generate substituted azomethine ylides in addition to the methods for the generation of unsubstituted azomethine ylides described in Scheme 1. These methods include, but are not limited to, pyrolysis of appropriately substituted aziridines, desilylation of α-trimethylsilylonium salts, etc. (for references, see *Synthesis*, 1973, 469; *Comprehensive Organic Synthesis*, Vol 4, B. M. Trost and I. Fleming, eds. Pergamon Press, New York, 1991; *Comprehensive Heterocyclic Synthesis*, Vol. 4, A. R. Katritzky and C. W. Rees, eds. Pergamon Press, New York, 1984). Thus, as shown in Scheme 4, additional compounds of Formula I can be prepared by [3+2] cycloaddition of intermediate 14, prepared as described previously, with an appropriate azomethine ylide to afford intermediate 15, where n and m are 1, and A and B are defined as in Formula I. Conversion of intermediate 15 to final compounds of Formula I follows the procedures described in Schemes 1 and 2.

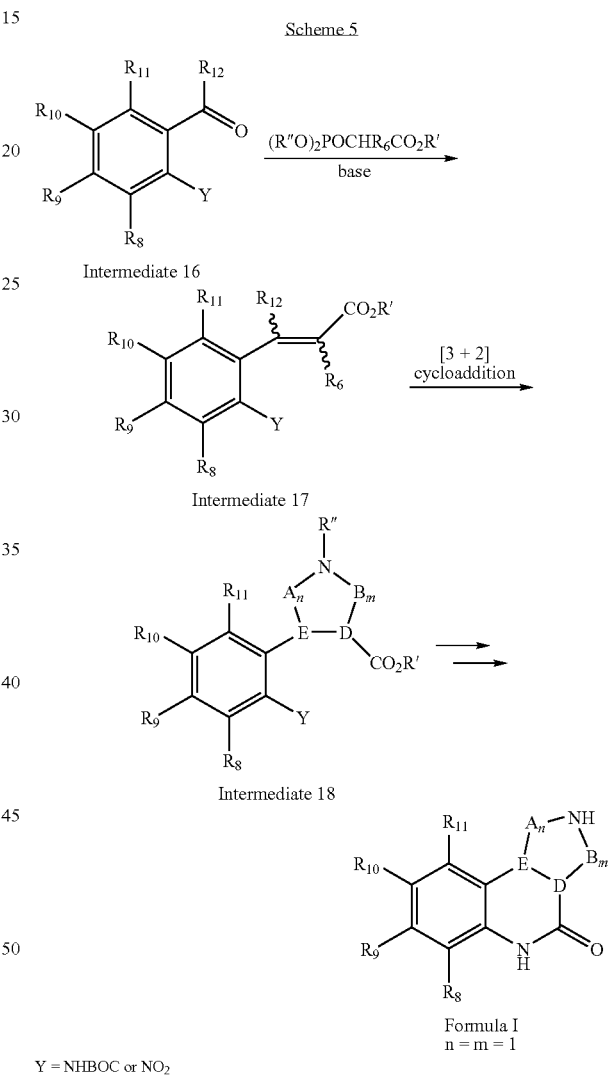

Compounds of Formula I, wherein n and m are 1, and D and E can be other than CH, and X=O, can be prepared as shown in Scheme 5. Readily available ketoester intermediates 16 can be treated with a wide variety of phosphonate reagents in the presence of an appropriate base, such as sodium hydride or KHMDS, to afford the olefin intermediate 17. As described in Schemes 1 and 2, different R'' groups on the phosphonate reagent can give rise to selective production of either the E- or Z-olefin 17. As described previously, intermediate 17 can be treated under a variety of conditions to effect a [3+2] cycloaddition to afford intermediate 18, where n and m are 1. Following procedures described previously, intermediate 18 can be converted to the Final compounds of Formula I.

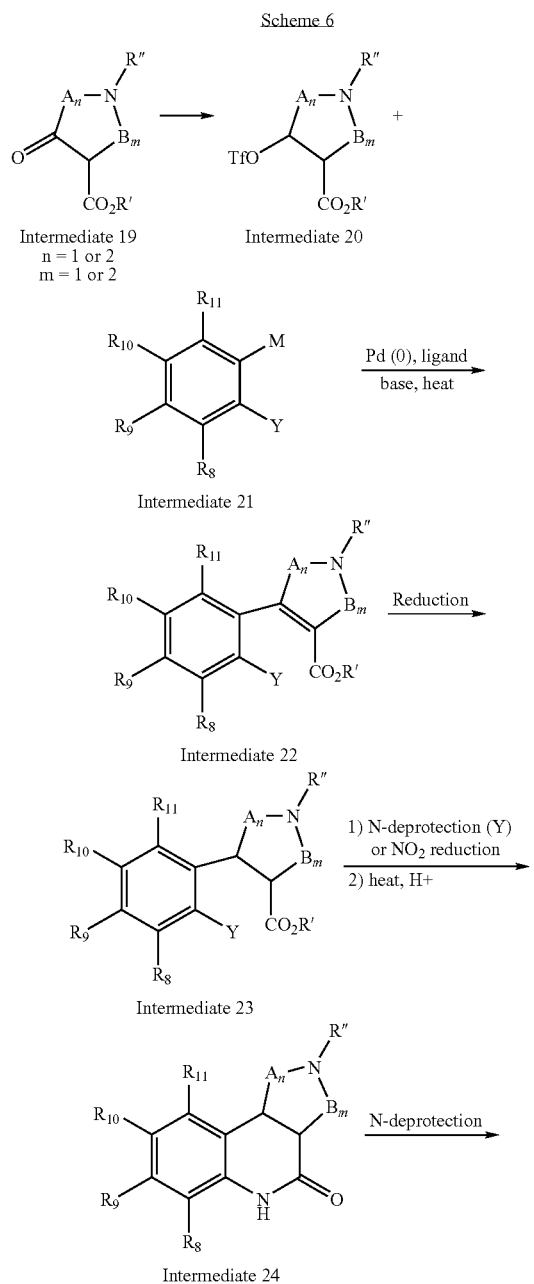

Y = NPG or NO2; M = B(OR)2 or SnR3

Compounds of Formula I, wherein D and E are CH, and X=O, can also be prepared as described in Scheme 6. A wide variety of cyclic ketoester intermediates 19 are well known in the chemical literature and are readily prepared by procedures known to those skilled in the art. Conversion of 19 to an enol triflate intermediate 20 is readily accomplished with trifluoromethanesulfonic anhydride or N-phenyltrifluoromethanesulfonimide and a base such as sodium hydride. Enol triflates 20 can be coupled with an appropriate, readily available aryl boronic acid or ester, or an aryl stannane reagent, intermediate 21, where NPG represents a suitable protecting group such as BOC (see also Greene, T and Wuts, P. G. M., *Protecting Groups in Organic Synthesis*, John Wiley & Sons, Inc., New York, N.Y., 1991), under a wide variety of palladium-catalyzed cross coupling conditions. For a review and leading references of palladium catalyzed cross coupling reactions, see Miyaura, N., Suzuki, A., *Chem. Rev.,* 1995, 2457; and J. Tsuji, "Palladium Reagents and Catalysts, Innovations in Organic Synthesis", J. Wiley and Sons, New York, 1995. One such procedure entails treatment of intermediate 20 with intermediate 21 in the presence of a catalytic Pd species, such as $Pd(PPh_3)_4$, $Pd(PPh_3)_2Cl2$, $Pd(OAc)_2$ or $Pd_2(dba)_3$ and a suitable ligand such as $PPh_3$, BINAP, etc., and a base such as NaOtBu, $Ba(OH)_2$ or $Na_2CO_3$ in a suitable solvent such as DMF, toluene, THF, or DME, to afford the intermediate 22. Reduction of intermediate 22 can be carried out to produce both the cis and trans relationship between the ester and aryl groups. Catalytic hydrogenation in the presence of a catalyst such as Pd/C affords the cis intermediates 23. Deprotonation of 23 with a base such as LDA, and allowing equilibration to take place produces a preponderance of the trans intermediates 23. Alternatively, reduction of intermediate 22 can be accomplished under a variety of 1,4-conjugate reduction conditions to afford variable mixtures of cis and trans intermediates 23 (for examples, see Jurkauskas, V. et. al.; *Org. Lett.* 2003, 5, 2417; Ranu, B., et. al.; *Tetrahedron Lett.* 2002, 43, 7405; *Syn. Commun.* 2003, 33, 291; and references cited therein). N-deprotection of the Y group (when Y=NPG; see Greene, T and Wuts, P. G. M., *Protecting Groups in Organic Synthesis*, John Wiley & Sons, Inc., New York, N.Y., 1991) or reduction of the nitro group (when $Y=NO_2$), followed by ring-closing condensation affords intermediate 24. The ring closure can occur spontaneously or under heating in a suitable solvent with or without an acid such as p-toluenesulfonic acid. It will also be noted by those skilled in the art that when $Y=NO_2$ in intermediate 22, certain olefin reduction conditions used to prepare intermediate 23 will also reduce the nitro group to the corresponding aniline, such that a separate step to reduce the nitro group may be unnecessary. N-deprotection of intermediate 24 as described previously affords compounds of Formula I, wherein n and m are 1 or 2, and X=O.

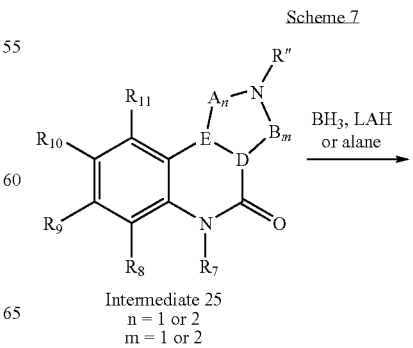

Scheme 7

Intermediate 25
n = 1 or 2
m = 1 or 2

-continued

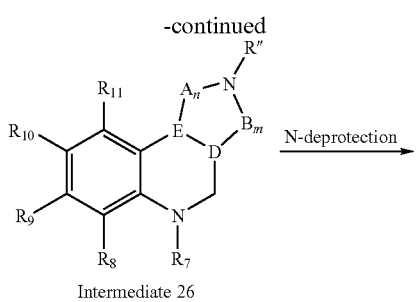

Intermediate 26

N-deprotection

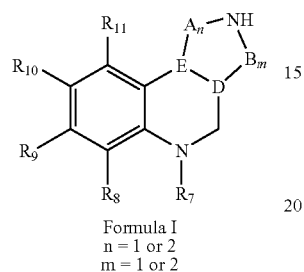

Formula I
n = 1 or 2
m = 1 or 2

Compounds of Formula I, wherein n and m are 1 or 2, and X=$H_2$, are prepared as shown in Scheme 7. Intermediate 25, where R" is an appropriate protecting group, such as N-benzyl, is treated with a reducing reagent, such as borane, lithium aluminum hydride or alane, in a solvent such as THF or ether, to effect the reduction of the lactam to afford intermediate 26. Standard N-deprotection affords compounds of Formula I wherein n and m are 1 or 2, and X=$H_2$.

Scheme 8

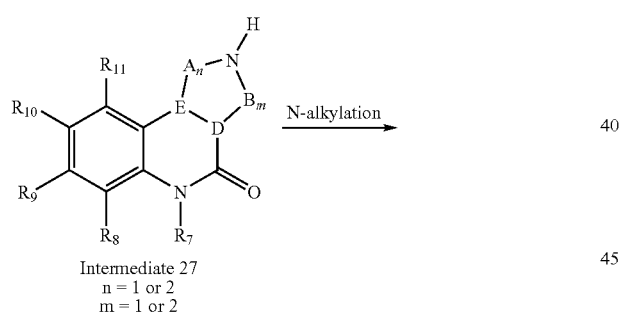

Intermediate 27
n = 1 or 2
m = 1 or 2

N-alkylation

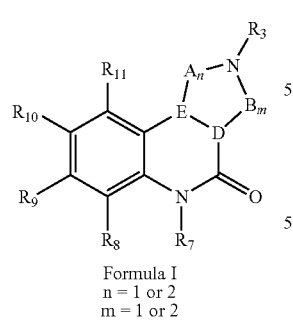

Formula I
n = 1 or 2
m = 1 or 2

Compounds of Formula 1, wherein n and m are 1 or 2, and in which R3 is other than H, are prepared as shown in Scheme 8. These compounds are prepared from intermediate 27 by reductive alkylation with an aldehyde or ketone under conditions known in the art, for example, catalytic hydrogenation with hydrogen in the presence of palladium or platinum or with reducing agents such as sodium triacetoxyborohydride. Alternatively, a similar transformation can be accomplished by treating intermediate 27 with an alkylating agent R3X, where X is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent to yield compounds of Formula I wherein R3 is not hydrogen.

Scheme 9

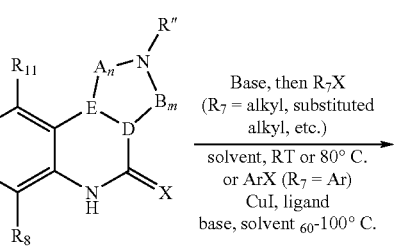

Intermediate 28
n = 1 or 2
m = 1 or 2

Base, then $R_7X$
($R_7$ = alkyl, substituted alkyl, etc.)
solvent, RT or 80° C.
or ArX ($R_7$ = Ar)
CuI, ligand
base, solvent $_{60}$-100° C.

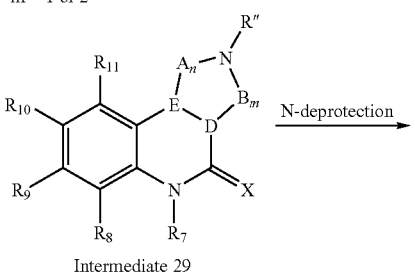

Intermediate 29

N-deprotection

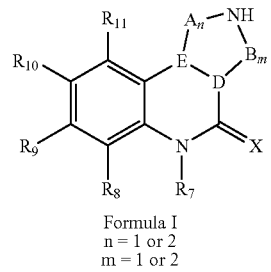

Formula I
n = 1 or 2
m = 1 or 2

Compounds of Formula I, wherein n and m are 1 or 2, and R7 is other than hydrogen, can be prepared as shown in Scheme 9. Treatment of intermediate 28, where R" is an appropriate N-protecting group, such as BOC, under a variety of N-alkylation or N-arylation conditions can afford N-alkyl or N-aryl intermediates 29. For example, for N-alkyl derivatives, treatment of intermediate 29 with a base such as sodium hydride followed by treatment of the resulting anion with a wide variety of alkylating agents, such as but not limited to alkyl halides R7X, where X=Br, I, Cl, OTs, etc., affords intermediate 29. For N-aryl derivatives, treatment of intermediate 28 with an aryl halide under copper or palladium catalysis can afford the intermediate 29. One preferred method uses an appropriate aryl iodide or aryl bromide, CuI and a diamine such as N,N'-dimethylethylenediamine as the catalyst system, and a base such as potassium phosphate in a solvent such as benzene or toluene at reflux temperature to afford the intermediates 29 (Buchwald, S.; et. al. *J. Am. Chem. Soc.* 2002, 124, 7421). N-deprotection of intermediate 29 under appropriate conditions then affords the compounds of Formula I where n and m are 1 or 2, and R7 is a group other than H.

Scheme 10

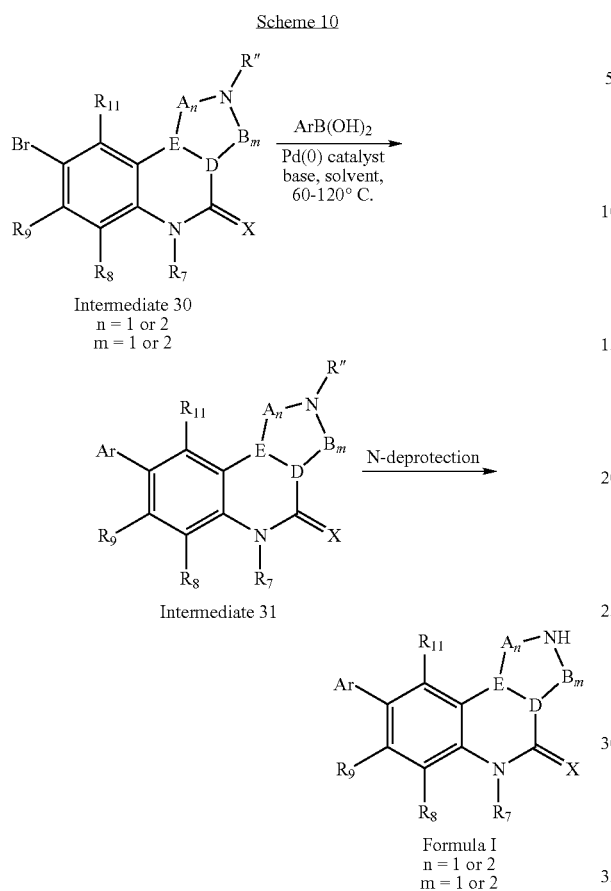

Intermediate 30
n = 1 or 2
m = 1 or 2

Intermediate 31

Formula I
n = 1 or 2
m = 1 or 2

Alternatively, compounds of Formula 1 can be further modified by the procedures outlined in Scheme 10. It is understood that the aromatic substitution is shown for only one position on the aromatic ring and that similar transformations may be performed at R8, R9, and R11. Compounds of Formula 1 can be brominated in one of two procedures, the choice of procedures will be readily apparent to one skilled in the art, in which the nitrogen is protected with an amine protecting group (R″) well familiar to those skilled in the art, and typical examples may be found in Greene, T and Wuts, P. G. M., *Protecting Groups in Organic Synthesis*, John Wiley & Sons, Inc., New York, N.Y., 1991 and references therein, and then treated with N-bromosuccinimide in a suitable solvent such as but not limited to DMF to yield intermediate 30. Alternatively, the compound can be treated with N-bromosuccinimide in a suitable solvent such as sulfuric acid, triflouroacetic acid, etc. and then the amine protected to yield intermediate 30. Intermediate 30 can then be modified to yield compounds of Formula 1 by biaryl couplings, which can be accomplished under Suzuki coupling protocols. For a review and leading references of palladium catalyzed cross coupling reactions, see Miyaura, N., Suzuki, A., *Chem. Rev.*, 1995, 2457. One such procedure entails treatment of intermediate 30 with a functionalized aryl boronic acid in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, Ba(OH)$_2$ or Et$_3$N in a suitable solvent such as DMF, toluene, THF, DME or the like, to afford intermediate 31. Removal of the protecting group, R″, with the appropriate reagents, well familiar to those skilled in the art, and typical examples may be found in Greene, T and Wuts, P. G. M., *Protecting Groups in Organic Synthesis*, John Wiley & Sons, Inc., New York, N.Y., 1991 and references therein, yields compounds of Formula I.

Scheme 11

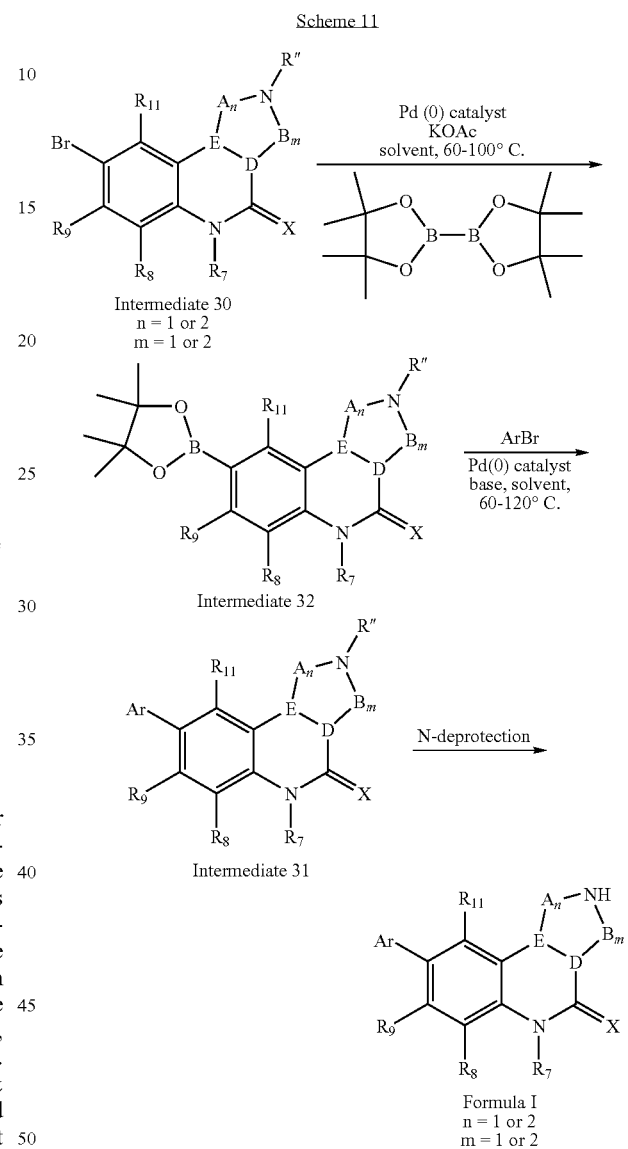

Intermediate 30
n = 1 or 2
m = 1 or 2

Intermediate 32

Intermediate 31

Formula I
n = 1 or 2
m = 1 or 2

Alternatively formation of the boronic ester from intermediate 30 would allow for greater diversity in the subsequent coupling of this boronic acid with commercially available haloaromatic derivatives in a similar Suzuki coupling strategy as described above to afford compounds of Formula 1. One such procedure is shown in Scheme 11, and it is understood that the aromatic substitution is shown for only one position on the aromatic ring and that similar transformations may be performed at R8, R9, and R11. Treatment of intermediate 30 with a palladium catalyst such as Pd(PPh$_3$)$_4$ or Pd(PPh$_3$)$_2$Cl$_2$ and a suitable base, a preferred one being potassium acetate, in the presence of diboron pinacol ester affords intermediate 32. This boronic ester can undergo Suzuki coupling directly with a wide variety of commercially available aryl bromides under typical Suzuki conditions as described in Scheme 10 to yield intermediate 31, which can be deprotected as described above to afford compounds of Formula 1.

Scheme 12

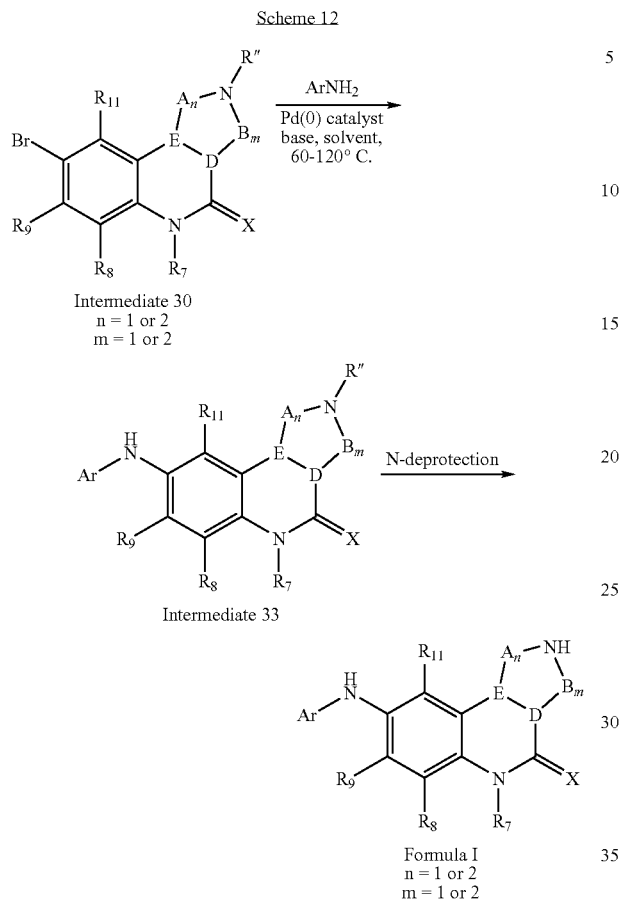

Compounds of Formula I with an arylamino group attached to the aromatic ring can be synthesized by the procedures outlined in Scheme 12, and it is understood that the aromatic substitution is shown for only one position on the aromatic ring and that similar transformations may be performed at R8, R9, R11. Treatment of intermediate 30 with a wide variety of commercially available anilines in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, etc. to yield intermediate 33, which can be deprotected as described above to afford compounds of Formula 1.

Scheme 13

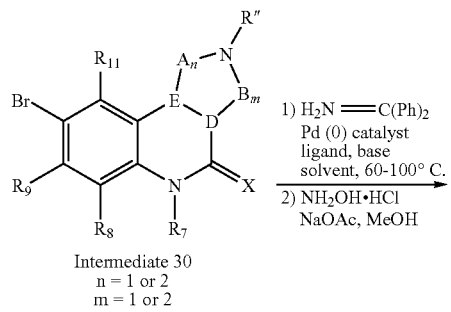

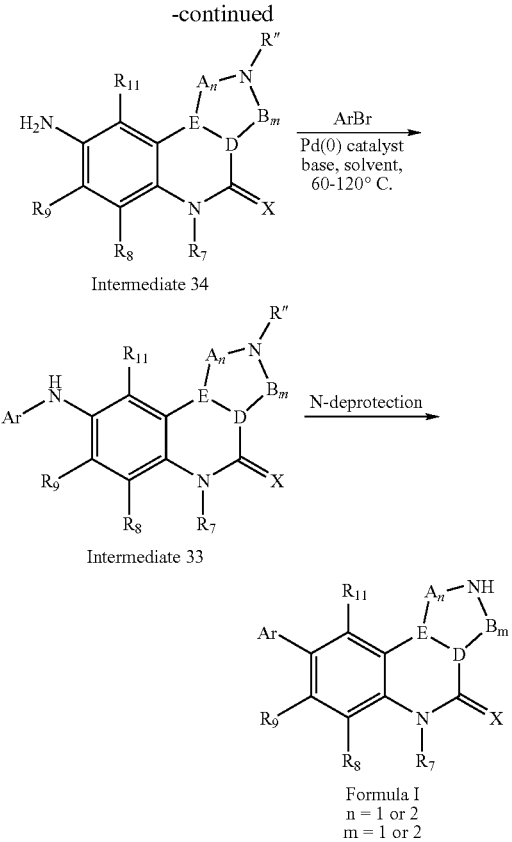

Alternatively, compounds of Formula I with an arylamino group attached to the aromatic ring can be synthesized by the procedures outlined in Scheme 13. Treatment of intermediate 30 with benzophenone imine in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, DME, etc., affords an imine in which nitrogen is attached to the aromatic ring. Hydrolysis of this imine, for example with hydroxylamine and sodium acetate in methanol, affords intermediate 34. This aniline can be treated with a wide variety of commercially available aryl bromides in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as but not limited to NaOtBu in a suitable solvent such as DMF, toluene, THF, DME, etc. to yield intermediate 33, which can be deprotected as described above to afford compounds of Formula 1.

Scheme 14

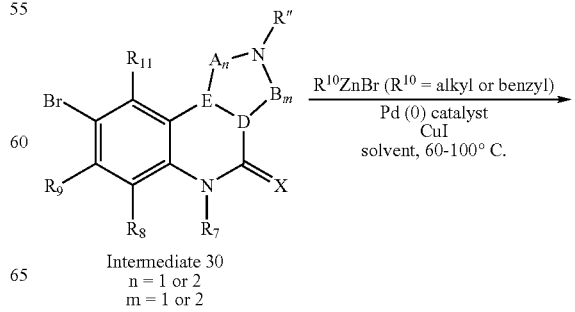

-continued

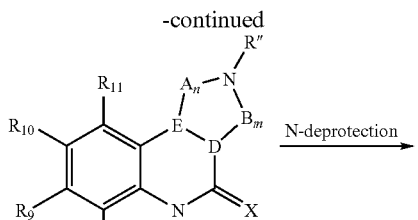

Intermediate 35
R = alkyl or benzyl

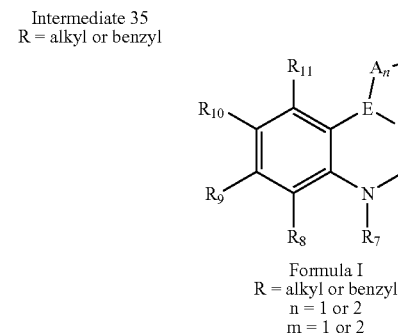

Formula I
R = alkyl or benzyl
n = 1 or 2
m = 1 or 2

Compounds of Formula I with benzyl or alkyl groups attached to the aromatic group can be prepared as shown in Scheme 14. Treatment of intermediate 30 with an appropriate benzylzinc or alkylzinc reagent, which can be generated from the corresponding benzyl halide, in the presence of a palladium (O) catalyst such as Pd(PPh$_3$)$_4$, Pd(PPh$_3$)$_2$Cl$_2$, or Pd$_2$(dba)$_3$, and with or without a copper (I) salt, affords intermediate 35 (see Knochel, et al. *Chem. Rev.* 1993, 93, 2117; and Weichert, et al. *Syn. Lett.* 1996, 473). This chemistry can also be extended to include a variety of alkylzinc and cycloalkylzinc reagents, which are available from the corresponding alkyl halides and cycloalkyl halides. The above intermediates can be deprotected as described above to afford compounds of Formula 1.

-continued

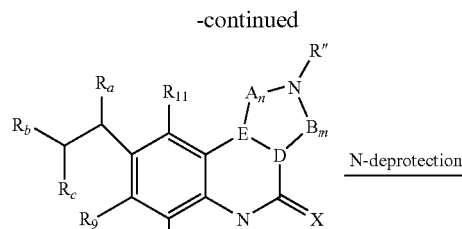

Intermediate 37

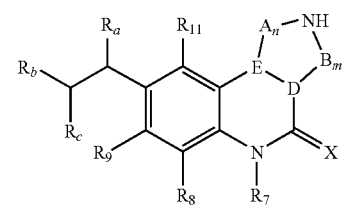

Formula I
n = 1 or 2
m = 1 or 2

Alternatively, compounds of Formula I with alkyl groups attached to the aromatic group can be prepared as shown in Scheme 15. Treatment of intermediate 30 with an appropriate vinyl boronic acid, which are commercially available or can be prepared readily, for example from the corresponding vinyl Grignard reagent, in the presence of a palladium (O) catalyst such as Pd(PPh$_3$)$_4$, Pd(PPh$_3$)$_2$Cl$_2$, or Pd$_2$(dba)$_3$ and a base such as NaOtBu or Na$_2$CO$_3$ in a suitable solvent such as DMF, toluene, THF, DME/H$_2$O, etc., affords the vinyl intermediate 36. Reduction of the vinyl group, such as by catalytic hydrogenation over Pd/C catalyst, affords reduced intermediate 37. These intermediates can be deprotected as described above to afford compounds of Formula 1.

Scheme 15

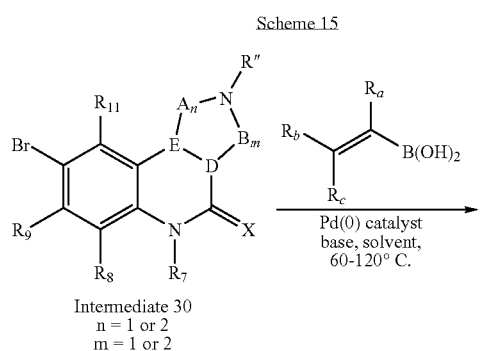

Intermediate 30
n = 1 or 2
m = 1 or 2

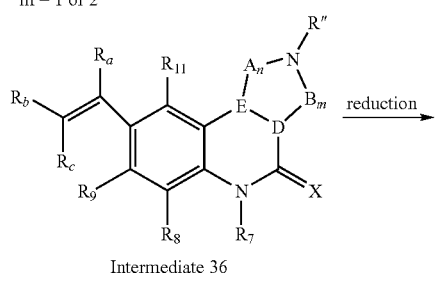

Intermediate 36

Scheme 16

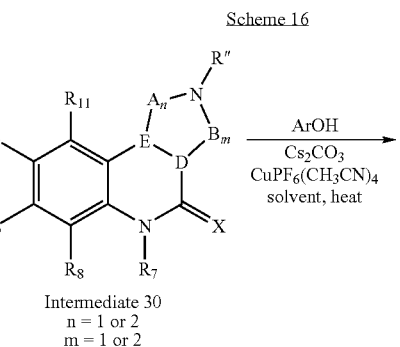

Intermediate 30
n = 1 or 2
m = 1 or 2

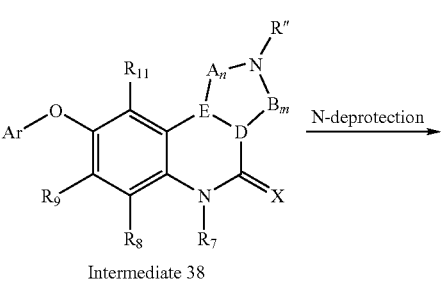

Intermediate 38

-continued

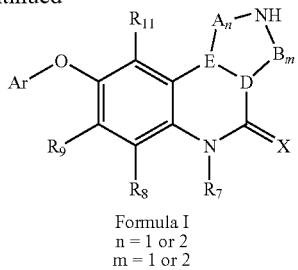

Formula I
n = 1 or 2
m = 1 or 2

Compounds of Formula I with an arylhydroxy group attached to the aromatic ring can be synthesized by the procedures outlined in Scheme 16, and it is understood that the aromatic substitution is shown for only one position on the aromatic ring and that similar transformations may be performed at R8, R9, R11. Intermediate 30 can be treated with various phenols in the presence of a base such as $Cs_2CO_3$, and a copper catalyst, such as $CuPF_6(CH_3CN)_4$, at elevated temperature to yield intermediate 38 (see Sawyer, *Tetrahedron* 2000, 56, 5045). The above intermediates can be deprotected as described above to afford compounds of Formula 1.

In addition, there exists a wide range of procedures and protocols for functionalizing haloaromatics, aryldiazonium and aryltriflate compounds. These procedures are well known by those in the art and described, for example, by Stanforth, *Tetrahedron*, 1998, 263; Buchwald et al., *J. Am. Chem. Soc.*, 1998, 9722; Stille, et al., *J. Am. Chem. Soc.*, 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

Utilities and Combinations

Utilities

The compounds of the present application are 5HT modulators, and include compounds which are, for example, selective agonists, partial agonists, antagonists or partial antagonists of the $5HT_{2C}$ receptor. Accordingly, the compounds of the present application may be useful for the treatment or prevention of diseases and disorders associated with 5HT receptor activity. Preferably, compounds of the present application possess activity as agonists of the $5HT_{2C}$ receptor, and may be used in the treatment of diseases or disorders associated with the activity of the $5HT_{2C}$ receptor.

Accordingly, the compounds of the present application can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, impaired glucose hemostatsis, insulin resistance, hypercholesterolemia, hypertriglyceridemia, cholelithiasis and sleep disorders, dislipidemic conditions, bulimia nervosa and compulsive eating disorders); pain; sleep disorders and psychiatric disorders, such as substance abuse, depression, anxiety, psychosis, mania and schizophrenia.

These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxininduced hypotension). These compounds could also be used for treatment of cardiac dysfunction (e.g., associated with valvular disease, myocardial infarction, cardiac hypertrophy or congestive heart failure); and improvement of the overall pulmonary function; transplant rejection; rheumatoid arthritis; osteoarthritis; fibromyalgia; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury. These compounds could also be used for treatment of sexual dysfunction and erectogenesis.

Compounds useful in the treatment of appetite or motivational disorders regulate desires to consume sugars, carbohydrates, alcohol or drugs and more generally to regulate the consumption of ingredients with hedonic value. In the present description and in the claims, appetite disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present application therefore further relates to the use of a $5HT_{2C}$ receptor agonist for the treatment of bulimia and obesity, including obesity associated with type II diabetes (non-insulin-dependent diabetes), or more generally any disease resulting in the patient becoming overweight. Overweight and obesity, as described herein, is defined by a body mass index ($kg/m^2$) for example, at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present application may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug, nicotine or alcohol withdrawal syndromes and substance-induced anxiety or mood disorder with onset during withdrawal.

Compounds in the present application may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, attention deficit-hyperactivity disorder, HIV, cardiovascular disease such as ischemia or stroke, and head trauma as well as age-related cognitive decline. Dementias are diseases that include memory loss and additional intellectual impairment separate from memory. 5HT$_{2C}$ modulators may also be useful in treating cognitive impairments related to attentional deficits, such as attention deficit-hyperactivity disorders.

Compounds in the present application may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, cognition enhancing agents, agents used to treat neurodegeneration, agents used to treat respiratory conditions, agents used to treat bowel disorders, anti-inflammatory agents; anti-anxiety agents; anti-depressants; anti-psychotic agents; sedatives; hypnotics; anti-hypertensive agents; anti-tumor agents and analgesics.

Such other therapeutic agent(s) may be administered prior to, simultaneously with, or following the administration of the 5HT$_{2C}$ modulators in accordance with the application.

Examples of suitable anti-obesity agents for use in combination with the compounds of the present application include leptin and leptin-sensitizing agents, melanocortin receptor (MC4R) agonists, agouti-related peptide (AGRP) antagonists, melanin-concentrating hormone receptor (MCHR) antagonists, growth hormone secretagogue receptor (GHSR) antagonists, orexin antagonists, CCK agonists, GLP-1 agonists, NPY1 or NPY5 antagonists, NPY2 modulators, corticotropin releasing factor agonists, histamine receptor-3 (H3) modulators, aP2 inhibitors, PPAR gamma modulators, PPAR delta modulators, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), leptinergics, adiponectin modulating agents, cannabinoid-1 receptor antagonists, such as SR-141716 (Sanofi) or SLV-319 (Solvay), acetyl CoA carboxylase (ACC) inhibitors as disclosed in International patent application WO 03/072197 and monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), axokine (Regeneron).

Examples of suitable anti-diabetic agents for use in combination with the compounds of the present application include: insulin, which may include short- and long-lasting forms as well as oral and inhaled forms, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists such as muraglitizar described in Bristol-Myers Squibb U.S. Pat. No. 6,414,002, dipeptidyl peptidase IV (DPP4) inhibitors such as saxagliptin described in Bristol-Myers Squibb U.S. Pat. Nos. 6,395,767 and 6,573,287, SGLT2 inhibitors such as the compounds described in Bristol-Myers Squibb U.S. Pat. Nos. 6,414,126 and 6,515,117, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be glucokinase inhibitors, 11 β HSD inhibitors or oral antihyperglycemic agents, which is preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (SankyolWL), NN-2344 (Dr. Reddy/NN), or YM-440 (Yamanouchi), preferably rosiglitazone and pioglitazone.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544, cyclopropanes reported by Capson, T. L., PhD dissertation, June, 1987, Dept. Med. Chem. U of Utah, Abstract, Table of Contents, pp 16, 17, 40-43, 48-51, Summary, pyrrolidine derivatives as disclosed by Sasyou, et al, WO 02/083636 and N-aryl-substituted cyclic amine derivatives disclosed by Okada et al, WO 02/076973.

Other hypolipidemic agents suitable for use herein include, but are not limited to, fibric acid derivatives, a PPAR agonists, such as fenofibrate, gemfibrozil, clofibrate, bezafibrate, ciprofibrate, clinofibrate and the like, probucol, and related compounds as disclosed in U.S. Pat. No. 3,674,836, probucol, phenylfibrate and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's Torcetrapib® as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof, and inhibitors or lipid synthesis enzymes such as, for example, ACC, FAS, DGAT, MGAT, GPAT, AMP kinase, CPT1 and SCD1. Preferred dislipidemic agents are pravastatin, lovastatin, simvastatin, atorvastatin, fluvastatin, pitavastatin, rosuvastatin, fenofibrate and Pfizer's Torcetrapib® as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan, candasartan and talmisartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

$5HT_{2C}$ modulators could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor agonists, ML 1 B agonists. GABA A receptor agonists such as barbiturates (e.g., amobarbital, aprobarbital, butabarbital, mephobarbital, pentobarbital, phenobarbital, secobarbital and talbutal), benzodiazepines (e.g., diazepam, lorazepam, oxazepam, alprazolam, chlordiazepoxide, clonazepam, chlorazepate, halazepam and prazepam), also specifically including triazolam (Halcion). Other agents for treating sleep disorders include zolpidem (Ambien) and Neurocrine's indiplon.

$5HT_{2C}$ modulators may reduce or ameliorate substance abuse or addictive disorders. Therefore, combination of $5HT_{2C}$ modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion and opiate antagonists.

$5HT_{2C}$ modulators may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), $5HT_{1A}$ receptor agonists (e.g., buspirone, flesinoxan, gepirone, ipsapirone and serzone), corticotropin releasing factor (CRF) antagonists and SSRI's.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine, citalopram and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists (Britsol-Myers Squibb U.S. Pat. Nos. 6,642,230; 6,630,476; 6,589,952; 6,579,876; 6,525,056; 6,521,636; 6,518,271; 6,515,005; 6,448,261; 6,399,609; 6,362,180; and 6,358,950), alpha-adrenoreceptor antagonists, and atypical antidepressants (bupropion, lithium, nefazodone, trazodone and viloxazine).

The combination of a conventional antipsychotic drug with a $5HT_{2C}$ modulator could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, $5HT_{2A}$ receptor antagonists and $5HT_{2A}$/dopamine receptor antagonists or partial agonists (e.g., olanzepine, aripiprazole, risperidone, ziprasidone).

The compounds described in the present application could be used to enhance the effects of cognition-enhancing agents, such as acetylcholinesterase inhibitors (e.g., tacrine the active agent in Cognex®), ADHD agents (e.g. methyl-phenidate, atomoxetine the active agent in Strattera® and histamine 3 antagonists), muscarinic receptor-1 agonists (e.g., milameline), nicotinic agonists, glutamic acid receptor (AMPA and NMDA) modulators such as memantine, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6 receptor antagonists, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present application could be used in combination with agents used to treat erectile dysfunction. Examples of suitable treatment for erectile dysfunction include sildenafil (Viagra), vardenafil (Levitra) and tadalafil (Cialis). Other compounds that could be used in combination for erectile dysfunction include yohimbine, phentolamine and papaverine.

The compounds described in the present application could be used in combination with suitable anti-inflammatory agents. Examples of suitable anti-inflammatory agents for use in combination with the compounds of the present application include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1 inhibitor, tumor necrosis factor (TNF) antagonists (e.g., infliximab, OR1384, including TNF-alpha inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with $5HT_{2C}$ modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., Et Al, "Cleavable CD40Ig Fusion Proteins and the Binding to Sgp39", J. Immunol. Methods (Netherlands), 188(1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", EMBO J. (England), 11(12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," New England J. of Medicine, 337(3), pp. 141-147 (1997).

The above other therapeutic agents, when employed in combination with the compounds of the present application, may be used, for example, in those amounts indicated in the Physicians' Desk Reference (PDR) or as otherwise determined by one of ordinary skill in the art.

The compounds of formula I of the application can be administered orally or parenterally, such as subcutaneously or intravenously, as well as by nasal application, transdermally, rectally or sublingually to various mammalian species known to be subject to such maladies, e.g., humans, in an effective amount within the dosage range of about 0.2 to 1000 mg, preferably from about 1 to 100 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intracisternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Pharmacological Analysis

The pharmacological analysis of each compound for either antagonism or agonism of $5\text{-}HT_{2A}$, $5\text{-}HT_{2B}$ and $5\text{-}HT_{2C}$ receptors consisted of in vitro and in vivo studies. In vitro analyses included $K_i$ determinations at $5\text{-}HT_{2A}$, $5\text{-}HT_{2B}$ and $5\text{-}HT_{2C}$ receptors and an assessment of functional (i.e., agonism or antagonism) activity at each receptor class by IP3 hydrolysis assays. Additional receptor assays were conducted to evaluate receptor specificity of $5\text{-}HT_{2C}$ receptors over monoamine and nuisance receptors (e.g. histamine, dopamine, and muscarinic). A compound is considered active as a $5\text{-}HT_2$ agonist if it has an $EC_{50}$ value or a $K_i$ value of less than about 50 micromolar; preferably less than about 1.0 micromolar; more preferably less than about 0.1 micromolar. Using the assays disclosed herein, compounds of the present application have been shown to have an $EC_{50}$ value of less than about 50 micromolar for $5\text{-}HT_2$ agonism.

In vivo assays assessed compound activity in a variety of behavioral paradigms including acute and chronic feeding models, anxiety and depression models (learned-helplessness, elevated plus maze, Geller-Siefter, conditioned taste aversion, taste reactivity, satiety sequence). In aggregate, these models reflect activity as a $5\text{-}HT_{2C}$ agonist (feeding models, anxiety models, depression models) and provide some indication as to bioavailability, metabolism and pharmacokinetics.

Radioligand binding experiments were conducted on recombinant human $5\text{-}HT_{2A}$, $5\text{-}HT_{2B}$, and $5\text{-}HT_{2C}$ receptors expressed in HEK293E cells. The affinities of compounds of the present application to bind at these receptors is determined by their capacity to compete for $[^{125}I]$-1-(2,5-dimethoxy-4-iodophenyl)-2-amino-propane (DOI) or $[^3H]$-lysergic acid diethylamide (LSD) binding at the $5\text{-}HT_{2A}$, $5\text{-}HT_{2B}$, or $5\text{-}HT_{2C}$ receptors. General references for binding assays include 1) Lucaites V L, Nelson D L, Wainscott D B, Baez M (1996) Receptor subtype and density determine the coupling repertoire of the $5\text{-}HT_2$ receptor subfamily. Life Sci., 59(13):1081-95. Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of $5\text{-}HT_2$ serotonin receptors. J. Med. Chem. (1988) 31(1):5-7 and 3 Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328-35.

The functional properties of compounds (efficacy and potency) were determined in whole cells expressing $5\text{-}HT_{2A}$, $5\text{-}HT_{2B}$, or $5\text{-}HT_{2C}$ receptors by assessing their ability to stimulate or inhibit receptor-mediated phosphoinositol hydrolysis and/or intracellular calcium release. The procedures used are described below.

In Vitro Binding Assays

Stable Expression of $5\text{-}HT_{2A}$, $5\text{-}HT_{2B}$ and $5\text{-}HT_{2C}$ Receptors in HEK293E Cells
Stable cell lines were generated by transfecting 293EBNA cells with plasmids containing human $5\text{-}HT_{2A}$, $5\text{-}HT_{2B}$, or $5\text{-}HT_{2C}$ receptor (INI, INV, VNV or VGV RNA-edited isoforms) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The $5\text{-}HT_2A$ cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation
On the day of assay, pellets of whole cells (containing approximately $1\times10^8$ cells) expressing the $5\text{-}HT_{2A}$, $5\text{-}HT_{2B}$ or $5\text{-}HT_{2C}$ receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the $5\text{-}HT_{2A}$, $5\text{-}HT_{2B}$ and $5\text{-}HT_{2C}$ Receptors
Radioligand binding studies were conducted to determine the binding affinities (Ki values) of compounds for the human recombinant $5\text{-}HT_{2A}$, $5\text{-}HT_{2B}$, and $5\text{-}HT_{2C}$ receptors (Fitzgerald et al., 1999). Assays were conducted in disposable polypropylene 96-well plates (Costar Corp., Cambridge, Mass.) and were initiated by the addition of $5\text{-}HT_{2A}$, $5\text{-}HT_{2B}$, or $5\text{-}HT_{2C}$ membrane homogenate in tissue buffer (10-30 (g/well) to assay buffer (50 mM Tris HCl, 0.5 mM EDTA, 10 mM pargyline, 10 mM $MgSO_4$, 0.05% ascorbic acid, pH 7.5) containing $[^{125}I]DOI$ for the $5\text{-}HT_{2A}$ and $5\text{-}HT_{2C}$ receptors (0.3-0.5 nM, final) or $[^3H]LSD$ (1-2.0 nM, final) for the $5\text{-}HT_{2B}$ receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (Packard cell harvester; Perkin-Elmer) over GFB glass-fiber filters that had been pre-soaked in 0.3% polyethyleneimine. Filters were washed in ice-cold 50 mM Tris HCl buffer (pH 7.5) and then counted on a Top Count (Packard).

Phosphoinositide Hydrolysis Studies
The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human $5\text{-}HT_{2A}$, $5\text{-}HT_{2B}$, or $5\text{-}HT_{2C}$ receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250 (g/ml G418. Following a 24-48 hr period, the growth media was removed and replaced with DMEM without fetal calf serum and inositol (Gibco BRL). The cells were then incubated with DMEM. (without serum and inositol) containing a final concentration of 0.5 uCi/well myo-$[^3H]$ inositol for 16-18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Calcium Fluorescence Studies

The ability of newly synthesized compounds to stimulate calcium fluorescence was monitored in whole cells using a protocol described previously (Fitzgerlad et al., 1999). HEK293E cells expressing the human 5-HT$_2$C, or 5-HT$_{2B}$ receptor were lifted with 0.5 mM EDTA and plated at a density of 50,000/well onto poly-D-lysine-coated 96-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 µg/ml hygromycin B, and 250 µg/ml G418. Following a 24 hr period, the cell plates are removed from the incubator and an equal volume of Loading Buffer (Hanks BSS with 200 mM HEPES, pH 5.98) containing the calcium dye reagent (Fluo-3) is added to each well (100 µL per well for 96-well plates and then incubated for 1 hour at 37 C. Following the dye loading of the cells he plates are transferred to the FLIPR. Test compounds are added to the plate as a concentration response curve and the changes in fluorescence units due to calcium influx are monitored for a period of three seconds.

Data Analyses

The equilibrium apparent dissociation constants (Ki's) from the competition experiments were calculated using an iterative nonlinear regression curve-fitting program (Excelfit and TA Activity Base). For the PI hydrolysis and FLIPR experiments, EC50's were calculated using a one-site 'pseudo' Hill model: y=((Rmax−Rmin)/(1+R/EC50)nH))+Rmax where R=response (GraphPad Prism; San Diego, Calif.). Emax (maximal response) was derived from the fitted curve maxima (net EP stimulation) for each compound. Intrinsic activity (IA) was determined by expressing the Emax of a compound as a percentage of the Emax of 5-HT (IA=1.0).

Efficacy Models to Evaluate Food Consumption and Weight Loss

Acute overnight feeding assay. Compounds are assessed to for their ability to reduce food consumption during the dark cycle, which is the most active period of feeding in the rat. Fischer 344 rats are trained on a fixed ratio three (FR3) response paradigm which requires them to press a bar 3 consecutive times in order to obtain a food pellet. The number of bar presses occurring throughout the dark cycle can be monitored electronically as a measure of food intake by the animal. Rats are dosed orally or intraperitoneally with test compound 30 minutes prior to the onset of the dark cycle. The treated animals are then placed in individual operant boxes for 15 hours (12 hrs of dark cycle and the first three hours of the light cycle). Food intake in compound treated animals is compared to that of vehicle treated animals in order to determine percent reductions in food intake. Simultaneous measurements of water intake and locomotor activity are also measured during the period to assess for potential adverse effects.

Chronic Feeding Assay

Compounds are assessed for their long term impact on food intake and body weight in a three to fourteen week chronic treatment paradigm in Sprague-Dawley rats (starting weight ~450 g). Male Sprague-Dawley rats are pre-handled for one week prior to the onset of dosing during which time they are also assessed for food intake behavior. Rats are then assigned to treatment groups. Rats are dosed with vehicle or compound by oral gavage. The food intake and body weights are cumulatively assessed at the end of each treatment week and compared to vehicle treated animals. In some studies food intake is measured daily in order to assess the impact of reduced food consumption on pair-fed animals. At the end of the study period the animals are assessed for changes in body composition utilizing DEXA and are then sacrificed in order to examine changes in various blood plasma parameters.

REFERENCES

Arnt, J. Acta Pharmacol. et Toxicol. 1982: 51, 321-329.

Berridge M. J., Downes P. C., Hanley M. R. (1982) Lithium amplifies agonist-dependent phosphotidyinositol response in brain and salivary glands. Biochem. J., 206, 587-595.

Costall, B and Naylor, R J. Psychopharmacology. 1975: 43, 69-74.

Egan C. T., Herrick-Davis K., Miller K., Glennon R. A., and Teitler M. (1998) Agonist activity of LSD and lisuride at cloned 5-HT$_{2A}$ and 5-HT$_{2C}$ receptors. Psychopharmacology, 136, 409-414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT$_{2A}$ and 5-HT$_{2C}$ receptors: evidence favoring the ternary complex and two-state models of agonist action. J. Neurochem., 72, 2127-2134.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301-308.

Dosage and Formulations

The serotonin agonist and serotonin antagonist compounds of this application can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form. Further, they may also be administered by internasal delivery, transdermal delivery and suppository or depot delivery all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.01 to about 30 mg/kg. Advantageously, compounds of the present application may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this application can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

EXAMPLES

Example 1

(±)-cis-Ethyl 2-benzyl-4-oxo-6-(trifluoromethyl)-2,3,3a,4,5,9b-hexahydro-1H-pyrrolo[3,4-c]quinoline-3a-carboxylate hydrochloride

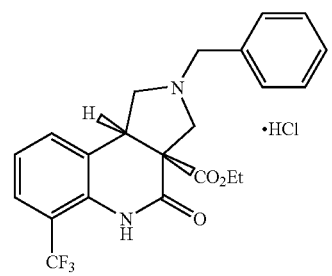

Part A. tert-Butyl 2-(trifluoromethyl)phenylcarbamate

To a solution of 1-isocyanato-2-(trifluoromethyl)benzene (4.0 g, 21.4 mmol) in 50 mL of THF at 0° C. was added potassium tert-butoxide (32.0 mL of a 1M solution in THF, 32 mmol) dropwise. The reaction was allowed to stir for 3 h with warming to ambient temperature and then was quenched with 10 mL of water. The mixture was diluted with ethyl acetate and the organics were washed sequentially with 1N HCl, sat'd. aq. NaHCO$_3$ and brine, dried (MgSO$_4$) and concentrated. The residue was taken up in chloroform, filtered through a pad of silica gel and concentrated to afford 2.9 g (52%) of the title compound which was sufficiently pure to be used without further purification. $^1$H NMR (CDCl$_3$): δ 8.13 (d, 1H, J=8.2 Hz), 7.56 (d, 1H, J=7.7 Hz), 7.52 (t, 1H, J=8.0 Hz), 7.14 (t, 1H, J=7.7 Hz), 6.80 (broad s, 1H), 1.53 (s, 9H).

Part B. tert-Butyl 2-formyl-6-(trifluoromethyl)phenylcarbamate

To a solution of tert-butyl 2-(trifluoromethyl)phenylcarbamate (1.0 g, 3.83 mmol) and N,N,N'N'-tetramethylethylenediamine (1.27 mL, 8.43 mmol) in 20 mL of anhydrous THF at −78° C. was added sec-butyllithium (8.43 mL of a 1.0 M solution in hexanes, 8.43 mmol) dropwise over 15 min. The reaction was stirred at −78° C. for 1 h and then there was added DMF (0.33 mL, 4.21 mmol). The reaction was stirred at −78° C. for 1 h and then was quenched with sat'd aq NH$_4$Cl (10 mL) and allowed to warm to ambient temperature. The reaction mixture was diluted with water and extracted with EtOAc. The organics were washed with 1N HCl and brine, dried (MgSO$_4$) and concentrated. The residue was purified by flash chromatography (230-400 mesh silica gel, elution with 6:1 hexane/EtOAc) to afford 0.4 g (36%) of the title compound. $^1$H NMR (CDCl$_3$): δ 10.06 (s, 1H), 8.07 (d, 1H, J=7.7 Hz), 7.83 (d, 1H, J=7.8 Hz), 7.43 (t, 1H, J=7.8 Hz), 6.83 (broad s, 1H), 1.47 (s, 9H). LRMS (ESI): 290.15 (M+H)+.

Part C. Diethyl 2-(2-(tert-butoxycarbonyl)-3-(trifluoromethyl)benzylidene)malonate To a solution of tert-butyl 2-formyl-6-(trifluoromethyl)phenylcarbamate (0.40 g, 1.40 mmol) in 10 mL of benzene was added diethyl malonate (0.21 mL, 1.40 mmol), piperidine (0.015 mL, 0.15 mmol) and benzoic acid (17 mg, 0.14 mmol). The resulting mixture was allowed to stir at 80° C. for 6 h while water was collected in a Dean-Stark trap. The reaction was allowed to cool and was diluted with EtOAc. The organics were washed with 1N HCl, sat'd aq NaHCO$_3$ and brine, dried (MgSO$_4$), filtered through a pad of silica gel and concentrated in vacuo to afford 0.58 g (96%) of the title compound as an oil which solidified on standing. $^1$H NMR (CDCl$_3$): δ 7.89 (s, 1H), 7.70-7.63 (m, 2H), 7.35 (t, 1H, J=7.7 Hz), 6.30 (broad s, 1H), 4.26-4.17 (m, 4H), 1.46 (s, 9H), 1.36-1.26 (m, 6H). LRMS (ESI): 432.32 (M+H)+.

Part D. (±)-cis-Ethyl 2-benzyl-4-oxo-6-(trifluoromethyl)-2,3,3a,4,5,9b-hexahydro-1H-pyrrolo [3,4-c]quinoline-3a-carboxylate To a solution of diethyl 2-(2-(tert-butoxycarbonyl)-3-(trifluoromethyl)benzylidene)malonate (188 mg, 0.44 mmol) in 5 mL of CH$_2$Cl$_2$ was added N-(methoxymethyl)-N-(trimethylsilylmethyl)benzylamine (115 mg, 0.48 mmol) and trifluoroacetic acid (0.0068 mL, 0.09 mmol). The solution was allowed to stir at 40° C. for 4 h. Starting material still remained by TLC analysis and so additional N-(methoxymethyl)-N-(trimethylsilylmethyl)benzylamine (115 mg, 0.48 mmol) and trifluoroacetic acid (0.0068 mL, 0.09 mmol) were added and the reaction was stirred at 40° C. for an additional 3 h. The reaction was allowed to cool to ambient temperature and then there was added trifluoroacetic acid (2 mL) and the reaction was allowed to stir at ambient temperature for 2 h. The reaction mixture was concentrated and diluted with EtOAc. The organics were washed with sat'd aq NaHCO$_3$ and brine, dried (MgSO$_4$), filtered through a pad of silica gel and concentrated in vacuo. The residue was purified by flash chromatography (230-400 mesh silica gel, elution with 6:1 hexane/EtOAc) to afford 70 mg (38%) of the title compound as an oil. $^1$H NMR (CDCl$_3$): δ 7.95 (broad s, 1H), 7.49 (d, 1H, J=7.9 Hz), 7.33-7.22 (m, 6H), 7.07 (t, 1H, J=7.7 Hz), 4.13 (dq, 2H, J=1.3, 7.0 Hz), 3.86 (t, 1H, J=8.8 Hz), 3.70 (s, 2H), 3.53 (ABq, 2H, J$_{AB}$=10.1 Hz), 3.18 (t, 1H, J=8.8 Hz), 2.57 (t, 1H, J=9.5 Hz), 1.10 (t, 3H, J=7.1 Hz). LRMS (ESI): 419.32 (M+H)+.

Part E. (±)-cis-Ethyl 2-benzyl-4-oxo-6-(trifluoromethyl)-2,3,3a,4,5,9b-hexahydro-1H-pyrrolo[3,4-c]quinoline-3a-carboxylate hydrochloride To a solution of (±)-cis-ethyl 2-benzyl-4-oxo-6-(trifluoromethyl)-2,3,3a,4,5,9b-hexahydro-1H-pyrrolo[3,4-c]quinoline-3a-carboxylate (20 mg, 0.048 mmol) in 3 mL of diethyl ether was added HCl (0.024 mL of a 4N solution in 1,4-dioxane, 0.096 mmol). A solid slowly settled out of solution. The solvents were decanted and the remaining solid was triturated twice with diethyl ether and dried in vacuo to afford 15 mg (68%) of the title compound of Example 1 as an off-white solid. LRMS (ESI): 419.32 (M+H)+.

Example 2

(±)-cis-2-Benzyl-6-(trifluoromethyl)-1,2,3,3a-tetrahydro-5H-pyrrolo[3,4-c]quinolin-4(9bH)-one hydrochloride

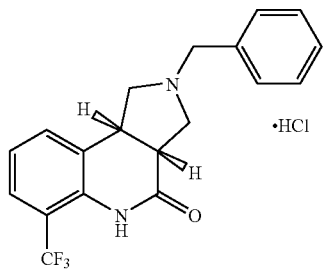

To a solution of (±)-cis-ethyl 2-benzyl-4-oxo-6-(trifluoromethyl)-2,3,3a,4,5,9b-hexahydro-1H-pyrrolo[3,4-c]quinoline-3a-carboxylate from Example 1, Part D (45 mg, 0.11 mmol) in 6 mL of 1,4-dioxane was added 4 mL of 3N HCl. The reaction was stirred at 90° C. for 18 h. The reaction was allowed to cool and was concentrated in vacuo. The residue was partitioned between ethyl acetate and sat'd aq NaHCO$_3$. The organics were washed with brine, dried (Na$_2$SO$_4$) and concentrated in vacuo. The residue was taken up in 3 mL of diethyl ether and then there was added HCl (0.10 mL of a 4N solution in 1,4-dioxane, 0.40 mmol). A solid settled out of solution. The solvents were decanted and the remaining solid was triturated twice with diethyl ether and dried in vacuo to afford 30 mg (73%) of the title compound of Example 2 as an off-white solid. LRMS (ESI): 347.26 (M+H)+.

Example 3

(±)-cis-6-(Trifluoromethyl)-1,2,3,3a-tetrahydro-5H-pyrrolo[3,4-c]quinolin-4(9bH)-one hydrochloride

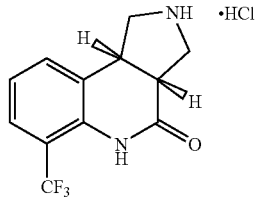

To a solution of (±)-cis-2-benzyl-6-(trifluoromethyl)-1,2,3,3a-tetrahydro-5H-pyrrolo[3,4-c]quinolin-4(9bH)-one from Example 2 (288 mg, 0.83 mmol) in 10 mL of methanol was added di-tert-butyl dicarbonate (182 mg, 0.83 mmol) and 10% Pd/C catalyst (29 mg, 10% by wt). The mixture was placed on a Parr shaker under 50 psi of hydrogen for 3 h. The reaction was filtered through a pad of Celite and concentrated in vacuo. The residue was purified by chromatography (ISCO, elution with 0-25% EtOAc in hexane) to afford 212 mg (72%) of the N-BOC derivative, (±)-cis-tert-butyl 4-oxo-6-(trifluoromethyl)-3,3a,4,5-tetrahydro-1H-pyrrolo[3,4-c]quinoline-2(9bH)-carboxylate. To a portion of this material (80 mg, 0.22 mmol) in 4 mL of diethyl ether was added HCl (4 mL of a 4N solution in 1,4-dioxane, 16 mmol) and the resulting solution was allowed to stir at ambient temperature overnight. The solvents were removed in vacuo and the resulting solid was triturated twice with diethyl ether and dried in vacuo to afford 40 mg (60%) of the title compound of Example 3 as an off-white solid. $^1$H NMR (CD$_3$OD) (all signals broad, all splitting masked): δ 7.72-7.62 (broad m, 2H), 7.30-7.20 (broad m, 1H), 4.18 (broad m, 1H), 3.94 (broad m, 1H), 3.79 (broad m, 1H), 3.69 (broad m, 1H), 3.56 (broad m, 1H), 3.01 (broad m, 1H). LRMS (ESI): 257.14 (M+H)+.

Example 4

(±)-cis-5-Methyl-6-(trifluoromethyl)-1,2,3,3a-tetrahydro-5H-pyrrolo[3,4-c]quinolin-4(9bH)-one

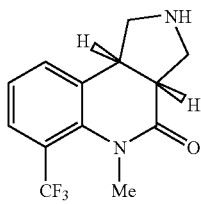

To a suspension of sodium hydride (40 mg of 60% dispersion in mineral oil, 1.0 mmol) in 5 mL of THF was added (±)-cis-tert-butyl 4-oxo-6-(trifluoromethyl)-3,3a,4,5-tetrahydro-1H-pyrrolo[3,4-c]quinoline-2(9bH)-carboxylate, the intermediate from Example 3 (80 mg, 0.22 mmol) in 3 mL of THF. The mixture was stirred for 30 min and then there was added iodomethane (0.10 mL, 1.6 mmol) and the resulting mixture was allowed to stir at ambient temperature for 18 h. The reaction was filtered through a pad of silica gel and concentrated. The residue was purified by chromatography (ISCO, elution with 1-10% EtOAc in hexane) to afford tert-butyl 5-methyl-4-oxo-6-(trifluoromethyl)-3,3a,4,5-tetrahydro-1H-pyrrolo[3,4-c]quinoline-2(9bH)-carboxylate. To this material in 4 mL of hexane was added HCl (4 mL of a 4N solution in 1,4-dioxane, 16 mmol) and the resulting solution was allowed to stir at ambient temperature overnight. The solvents were removed in vacuo and the residue was purified by HPLC (C18 reverse phase, elution with gradient H$_2$O/CH$_3$CN+0.5% TFA). Pure fractions were combined and concentrated. The residue was partitioned between aq NH$_4$OH and CHCl$_3$, the organics were washed with brine, dried (K$_2$CO$_3$) and concentrated to afford 12 mg (60%) of the title compound of Example 4. $^1$H NMR (CDCl$_3$): δ 7.60 (d, 1H), 7.42 (d, 1H), 7.18 (t, 1H), 3.81 (dd, 1H), 3.39 (s, 3H), 3.37-3.30 (m, 2H), 3.22-3.18 (m, 1H), 3.05-2.98 (m, 1H), 2.81 (t, 1H). LRMS (ESI): 271.16 (M+H)+.

Example 5

(±)-trans-2-Benzyl-6-(trifluoromethyl)-1,2,3,3a-tetrahydro-5H-pyrrolo[3,4-c]quinolin-4(9bH)-one hydrochloride

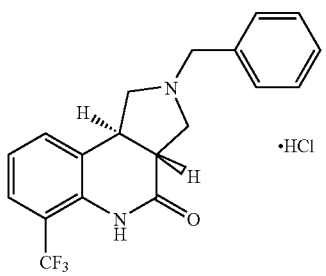

Part A. (E)-Ethyl 3-(2-(tert-butoxycarbonyl)-3-(trifluoromethyl)phenyl)acrylate

To a suspension of sodium hydride (288 mg of 60% dispersion in mineral oil, hexane-washed, 7.2 mmol) in 15 mL of THF was added ethyl dimethylphosphonoacetate (1.17 mL, 7.2 mmol) dropwise. The resulting mixture was allowed to stir at ambient temperature for 1 h. To this mixture was added tert-butyl 2-formyl-6-(trifluoromethyl)phenylcarbamate from Example 1, Part B (1.04 g, 3.60 mmol) as a solution in THF. The reaction was allowed to stir at ambient temperature for 18 h. The reaction was quenched with water and extracted with EtOAc. The organics were washed with brine, dried (MgSO$_4$) and concentrated in vacuo. The residue was purified by chromatography (ISCO, elution with 1-10% EtOAc in hexane) to afford 320 mg (25%) of the title compound.

Part B. (±)-trans-2-Benzyl-6-(trifluoromethyl)-1,2,3,3a-tetrahydro-5H-pyrrolo [3,4-c]quinolin-4(9bH)-one hydrochloride To a solution of (E)-ethyl 3-(2-(tert-butoxycarbonyl)-3-(trifluoromethyl)phenyl)acrylate (300 mg, 0.835 mmol) in 10 mL of CH$_2$Cl$_2$ was added N-(methoxymethyl)-N-(trimethylsilylmethyl)benzylamine (0.405 mL, 1.67 mmol) and trifluoroacetic acid (0.013 mL, 0.167 mmol). The solution was allowed to stir at 40° C. for 18 h.

Example 6

(±)-trans-6-(Trifluoromethyl)-1,2,3,3a-tetrahydro-5H-pyrrolo[3,4-c]quinolin-4(9bH)-one hydrochloride

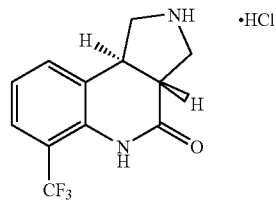

To a solution of (±)-trans-2-benzyl-6-(trifluoromethyl)-1,2,3,3a-tetrahydro-5H-pyrrolo[3,4-c]quinolin-4(9bH)-one from Example 5, Part B (30 mg, 0.087 mmol) in 10 mL of methanol was added HCl (0.25 mL of a 2M solution in ether, 0.5 mmol) and 10% Pd/C catalyst (10 mg). The resulting mixture was shaken in a Parr apparatus under 65 psi of hydrogen for 3 h. The reaction was filtered through a pad of Celite and concentrated in vacuo. The resulting solid was triturated several times with ether and dried in vacuo to afford 15 mg (60%) of the title compound of Example 6 as an off-white solid. $^1$H NMR (DMSO-D6): δ 10.09 (broad s, 1H), 9.90 (broad s, 1H), 9.69 (s, 1H), 7.61 (d, 1H), 7.50 (d, 1H), 7.24 (t, 1H), 3.95-3.88 (m, 1H), 3.52-3.38 (overlapping m, 2H), 3.32-3.20 (overlapping m, 2H), 3.08-2.98 (m, 1H). LRMS (ESI): 257.10 (M+H)+.

Example 7

(3aR,9bS)-6-(Trifluoromethyl)-1,2,3,3a-tetrahydro-5H-pyrrolo[3,4-c]quinolin-4(9bH)-one hydrochloride

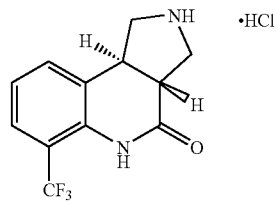

Part A. (±)-trans-tert-Butyl 4-oxo-6-(trifluoromethyl)-3,3a,4,5-tetrahydro-1H-pyrrolo[3,4-c]quinoline-2(9bH)-carboxylate To a solution of (±)-trans-2-benzyl-6-(trifluoromethyl)-1,2,3,3a-tetrahydro-5H-pyrrolo[3,4-c]quinolin-4(9bH)-one from Example 5, Part B (902 mg, 2.60 mmol) in 50 mL of methanol was added di-tert-butyl dicarbonate (625 mg, 2.86 mmol) and 10% Pd/C catalyst (90 mg, 10% by wt). The mixture was stirred under 1 atm of hydrogen, maintained by a balloon, for 5 h. The reaction was filtered through a pad of Celite and concentrated in vacuo. The residue was purified by chromatography (ISCO, elution with 0-40% EtOAc in hexane) to afford 395 mg (43%) of the title compound as a white solid. LRMS (ESI): 357 (M+H)+.

Part B. Chiral separation of (3aR,9bS)-tert-Butyl 4-oxo-6-(trifluoromethyl)-3,3a,4,5-tetrahydro-1H-pyrrolo[3,4-c]quinoline-2(9bH)-carboxylate and (3aS,9bR)-tert-Butyl 4-oxo-6-(trifluoromethyl)-3,3a,4,5-tetrahydro-1H-pyrrolo[3,4-c]quinoline-2(9bH)-carboxylate A sample of (±)-trans-tert-butyl 4-oxo-6-(trifluoromethyl)-3,3a,4,5-tetrahydro-1H-pyrrolo[3,4-c]quinoline-2(9bH)-carboxylate (395 mg) was separated into two eneatiomers using a Chiralcel AD column (elution with 5% isopropanol/heptane, flow rate 50 mL/min) to afford (3aR,9bS)-tert-butyl 4-oxo-6-(trifluoromethyl)-3,3a,4,5-tetrahydro-1H-pyrrolo[3,4-c]quinoline-2(9bH)-carboxylate (tentatively assigned as the first eluting compound) and (3aS,9bR)-tert-butyl 4-oxo-6-(trifluoromethyl)-3,3a,4,5-tetrahydro-1H-pyrrolo[3,4-c]quinoline-2(9bH)-carboxylate (tentatively assigned as the second eluting compound).

Part C. (3aR,9bS)-6-(Trifluoromethyl)-1,2,3,3a-tetrahydro-5H-pyrrolo[3,4-c]quinolin-4(9bH)-one hydrochloride To a solution of the first eluting compound from Part B above, tentatively assigned as (3aR,9bS)-tert-butyl 4-oxo-6-(trifluoromethyl)-3,3a,4,5-tetrahydro-1H-pyrrolo[3,4-c]quinoline-2(9bH)-carboxylate (50 mg, 0.14 mmol) in 4 mL of ether was added 1 mL of 12 N HCl. The resulting mixture was stirred at ambient temperature for 15 min and then was concentrated and dried in vacuo to a solid. This solid was triturated twice with ether and dried in vacuo to afford 30 mg (75%) of the title compound of Example 7 as a white solid. $^1$H NMR (DMSO-D6): δ 9.73 (s, 1H), 9.65 (broad s, 1H), 9.53 (broad s, 1H), 7.62 (d, 1H), 7.50 (d, 1H), 7.25 (t, 1H), 3.95-3.88 (m, 1H), 3.55-3.42 (overlapping m, 2H), 3.32-3.22 (overlapping m, 2H), 3.10-3.00 (m, 1H). LRMS (ESI): 257.2 (M+H)+.

Example 8

(3aS,9bR)-6-(Trifluoromethyl)-1,2,3,3a-tetrahydro-5H-pyrrolo[3,4-c]quinolin-4(9bH)-one hydrochloride

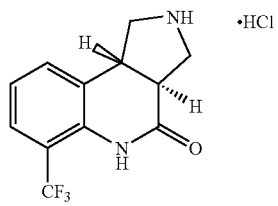

To a solution of the second eluting compound from Example 7, Part B, tentatively assigned as (3aS,9bR)-tert-butyl 4-oxo-6-(trifluoromethyl)-3,3a,4,5-tetrahydro-1H-pyrrolo[3,4-c]quinoline-2(9bH)-carboxylate (50 mg, 0.14 mmol) in 4 mL of ether was added 1 mL of 12 N HCl. The resulting mixture was stirred at ambient temperature for 15 min and then was concentrated and dried in vacuo to a solid. This solid was triturated twice with ether and dried in vacuo to afford 35 mg (85%) of the title compound of Example 8 as a white solid. $^1$H NMR (DMSO-D6): δ 9.73 (s, 1H), 9.66 (broad s, 1H), 9.54 (broad s, 1H), 7.62 (d, 1H), 7.50 (d, 1H), 7.25 (t, 1H), 3.96-3.90 (m, 1H), 3.55-3.42 (overlapping m, 2H), 3.32-3.22 (overlapping m, 2H), 3.10-3.00 (m, 1H). LRMS (ESI): 257.2 (M+H)+.

Example 9

(±)-cis 6-Methoxy-1,2,3,3a-tetrahydro-5H-pyrrolo[3,4-c]quinolin-4(9bH)-one

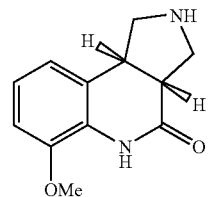

Part A. Diethyl 1-benzyl-4-(3-methoxy-2-nitrophenyl)pyrrolidine-3,3-dicarboxylate To a solution of diethyl 2-(3-methoxy-2-nitrobenzylidene)malonate, which was prepared from 3-methoxy-2-nitrobenzaldehyde following the procedure described in Example 1, Part C (162 mg, 0.5 mmol) in 10 mL of methylene chloride was added added N-(methoxymethyl)-N-(trimethylsilylmethyl)benzylamine (237 mg, 1.0 mmol) and trifluoroacetic acid (0.010 mL, 0.125 mmol). The solution was allowed to stir at 40° C. for 18 h. The reaction mixture was concentrated in vacuo and purified by flash chromatography (elution with 4:1 hexane/EtOAc) to afford 201 mg (88%) of the title compound. $^1$H NMR (CDCl$_3$): δ 7.40-7.25 (m, 7H), 6.93-6.85 (m, 1H), 4.36-4.30 (m, 1H), 4.32-4.15 (m, 2H), 3.87 (s, 3H), 3.77 (q, 2H), 3.69 (s, 2H), 3.60-3.50 (m, 1H), 3.05-2.97 (m, 1H), 2.85-2.78 (m, 1H), 2.75-2.68 (m, 1H), 1.23 (t, 3H, J=7.2 Hz), 0.83 (t, 3H, J=7.2 Hz). LRMS (ESI): 457.4 (M+H)+.

Part B. (±)-cis Ethyl 6-methoxy-4-oxo-2,3,3a,4,5,9b-hexahydro-1H-pyrrolo[3,4-c]quinoline-3a-carboxylate To a solution of diethyl 1-benzyl-4-(3-methoxy-2-nitrophenyl)pyrrolidine-3,3-dicarboxylate (200 mg, 0.44 mmol) in 20 mL of methanol was added 10% Pd/C catalyst (40 mg, 20% by wt). The mixture was placed on a Parr shaker under 50 psi of hydrogen for 18 h. The reaction was filtered through a pad of Celite and concentrated in vacuo. The residue was purified by flash chromatography (elution with 5% methanol/methylene chloride) to afford 77 mg (60%) of the title compound as a solid. LRMS (ESI): 291.2 (M+H)+.

Part C. (±)-cis 6-Methoxy-1,2,3,3a-tetrahydro-5H-pyrrolo[3,4-c]quinolin-4(9bH)-one To a solution of (±)-cis ethyl 6-methoxy-4-oxo-2,3,3a,4,5,9b-hexahydro-1H-pyrrolo[3,4-c]quinoline-3a-carboxylate (70 mg, 0.24 mmol) in 10 mL of 1,4-dioxane was added 10 mL of 3N HCl. The reaction was stirred at 90° C. for 18 h. The reaction was allowed to cool and was concentrated in vacuo. The residue was partitioned between ethyl acetate and sat'd aq NaHCO$_3$. The organics were washed with brine, dried (Na$_2$SO$_4$) and concentrated in vacuo. The residue was purified by prep HPLC (C18 reverse phase column, elution with a H$_2$O/CH$_3$CN gradient with 0.5% TFA) to afford the TFA salt. This material was free-based by partitioning between methylene chloride and aq. ammonium hydroxide. The organics were washed with brine, dried (Na$_2$SO$_4$) and concentrated to afford the title compound of Example 9 as a solid. $^1$H NMR (DMSO-D6): δ 9.63 (broad s, 1H), 9.30 (very broad s, 1H), 7.05-6.96 (m, 2H), 6.95-6.87 (m, 1H), 3.86-3.80 (m, 1H), 3.81 (s, 3H), 3.70-3.40 (overlappiing m, 4H), 2.77-2.69 (m, 1H). LRMS (ESI): 219.2 (M+H)+.

Example 10

(±)-cis 6-Methoxy-2,3,3a,4,5,9b-hexahydro-1H-pyrrolo[3,4-c]quinoline

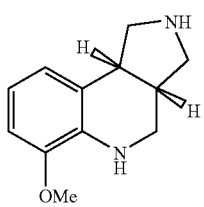

Part A. (±)-cis tert-Butyl 6-methoxy-4-oxo-3,3a,4,5-tetrahydro-1H-pyrrolo[3,4-c]quinoline-2(9bH)-carboxylate To a solution of (±)-cis ethyl 6-methoxy-4-oxo-2,3,3a,4,5,9b-hexahydro-1H-pyrrolo[3,4-c]quinoline-3a-carboxylate from Example 9, Part B (1.3 g, 4.5 mmol) in 25 mL of 1,4-dioxane was added 25 mL of 3 N HCl. The reaction was stirred at 90° C. for 24 h. The reaction was cooled to 0° C. and then there was added 25 mL of 5 N NaOH dropwise, followed by addition of di-tert-butyl dicarbonate (2.0 g, 9.2 mmol). The reaction mixture was allowed to stir at ambient temperature for 18 h. The reaction was diluted with ethyl acetate. The organics were washed with water and brine, dried (Na$_2$SO$_4$) and concentrated in vacuo to afford the title compound which was used without purification.

Part B. (±)-cis tert-Butyl 6-methoxy-3,3a,4,5-tetrahydro-1H-pyrrolo[3,4-c]quinoline-2(9bH)-carboxylate To a solution of (±)-cis tert-butyl 6-methoxy-4-oxo-3,3a,4,5-tetrahydro-1H-pyrrolo[3,4-c]quinoline-2(9bH)-carboxylate (1.4 g, 4.5 mmol) in 30 mL of THF at 0° C. was added borane THF complex (20 mL of a 1 M solution in THF, 20 mmol) dropwise. The reaction was allowed to warm to ambient temperature and was stirred for 2 h. The reaction was quenched carefully with water and extracted with ethyl acetate. The organics were washed with brine, dried (Na$_2$SO$_4$) and concentrated in vacuo. The residue was purified by flash chromatography to afford 1.26 g (92%) of the title compound. $^1$H NMR (CDCl$_3$) (some signals doubled due to rotamers): δ 6.68-6.55 (overlapping m, 3H), 4.42 (broad s, 1H), 3.95-3.82 (m, 1H), 3.78 (s, 3H), 3.64-3.55 (m, 1H), 3.38-3.15 (overlapping m, 4H), 3.02-2.92 (m, 1H), 2.52-2.42 (m, 1H), 3.63 and 3.61 (s, 9H).

Part C. (±)-cis 6-Methoxy-2,3,3a,4,5,9b-hexahydro-1H-pyrrolo[3,4-c]quinoline.

To a solution of (±)-cis tert-butyl 6-methoxy-3,3a,4,5-tetrahydro-1H-pyrrolo[3,4-c]quinoline-2(9bH)-carboxylate (25 mg, 0.082 mmol) in 4 mL methylene chloride was added 1 mL trifluoroacetic acid. The reaction was allowed to stir at ambient temperature for 2 h and then was concentrated in vacuo to afford a TFA salt. This material was free-based by partitioning between methylene chloride and aq. ammonium hydroxide. The organics were washed with brine, dried (Na$_2$SO$_4$) and concentrated to afford 10 mg (60%) of the title compound of Example 10. $^1$H NMR (CDCl$_3$): δ 6.76-6.62 (m, 3H), 4.42 (broad s, 1H), 3.85 (s, 3H), 3.50-3.23 (overlapping m, 5H), 2.98-2.80 (m, 2H), 2.65-2.57 (m, 1H). LRMS (ESI): 205.3 (M+H)+.

Example 11

(±)-cis 8-Bromo-6-methoxy-2,3,3a,4,5,9b-hexahydro-1H-pyrrolo[3,4-c]quinoline

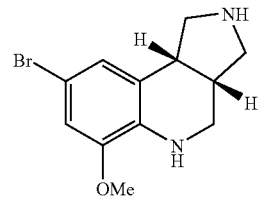

Part A. (±)-cis-tert-Butyl 8-bromo-6-methoxy-3,3a,4,5-tetrahydro-1H-pyrrolo [3,4-c]quinoline-2(9bH)-carboxylate To a solution of (±)-cis tert-butyl 6-methoxy-3,3a,4,5-tetrahydro-1H-pyrrolo[3,4-c]quinoline-2(9bH)-carboxylate from Example 10, Part B (0.39 g, 1.28 mmol) in 8 mL of THF and 4 mL of DMF at –30° C. was added N-bromosuccinimide (0.15 g, 1.34 mmol). The reaction was stirred at –30° C. for 1 h and then was diluted with water and ethyl acetate. The organics were washed with water and brine, dried (Na$_2$SO$_4$) and concentrated in vacuo to afford 0.41 g (83%) of the title compound which was used without purification.

Part B. (±)-cis 8-Bromo-6-methoxy-2,3,3a,4,5,9b-hexahydro-1H-pyrrolo[3,4-c]quinoline Following the procedure described in Example 10, Part C, (±)-cis-tert-butyl 8-bromo-6-methoxy-3,3a,4,5-tetrahydro-1H-pyrrolo[3,4-c]quinoline-2(9bH)-carboxylate was converted into the title compound of Example 11. LRMS (ESI): 283.2/285.2 (M+H)+.

Example 12

(±)-cis 6-Methoxy-8-phenyl-2,3,3a,4,5,9b-hexahydro-1H-pyrrolo[3,4-c]quinoline

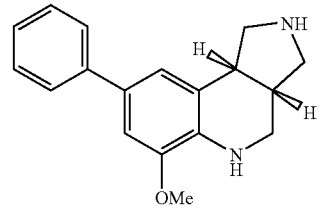

To a solution of (±)-cis-tert-butyl 8-bromo-6-methoxy-3,3a,4,5-tetrahydro-1H-pyrrolo[3,4-c]quinoline-2(9bH)-carboxylate from Example 11, Part A (50 mg, 0.13 mmol) in 10 mL of 1:1 DME/H$_2$O was added phenylboronic acid (32 mg, 0.26 mmol) and sodium carbonate (42 mg, 0.39 mmol). The mixture was degassed with a stream of argon for 15 min and then there was added [1,1'-bis(diphenylphosphino)ferrocene]dichloropalladium (II) (2 mg, 0.0026 mmol) and the mixture was stirred at 80° C. overnight. The reaction was cooled, diluted with ethyl acetate, washed with brine, dried (MgSO$_4$) and concentrated. The residue was purified on a prepacked silica gel tube (elution with hexanes to 1:1 hexanes/ethyl acetate) to remove catalyst and excess boronic acid. The residue was dissolved in 10 mL of methylene chloride and then there was added 2 mL of trifluoroacetic acid. The mixture was stirred for 3 h and concentrated in vacuo. The residue was purified by preparative HPLC (C18 reverse phase column, elution with a H$_2$O/CH$_3$CN gradient with 0.5% TFA) to afford the TFA salt. This material was free-based by partitioning between methylene chloride and aq. ammonium hydroxide. The organics were washed with brine, dried (Na$_2$SO$_4$) and concentrated to afford the title compound of Example 12. $^1$H NMR (CDCl$_3$): δ 7.58-7.50 (m, 2H), 7.47-7.38 (m, 2H), 7.33-7.25 (m, 1H), 6.95 (s, 1H), 6.90 (s, 1H), 4.51 (broad s, 1H), 3.91 (s, 3H), 3.72-3.65 (m, 1H), 3.52-3.42 (m, 2H), 3.38-3.28 (m, 1H), 3.12-2.98 (m, 3H), 2.74-2.66 (m, 1H). LRMS (ES)$^+$: 281.3 (M+H)$^+$.

Example 13

(±)-cis 6-Methoxy-8-(2-(trifluoromethyl)phenyl)-2,3,3a,4,5,9b-hexahydro-1H-pyrrolo [3,4-c]quinoline

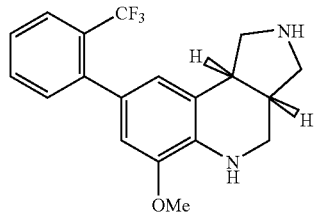

Following the procedures described in Example 12, except that 2-(trifluoromethyl)phenylboronic acid was used instead of phenylboronic acid, (±)-cis-tert-butyl 8-bromo-6-methoxy-3,3a,4,5-tetrahydro-1H-pyrrolo[3,4-c]quinoline-2 (9bH)-carboxylate from Example 11, Part A was converted into the title compound of Example 13. $^1$H NMR (CDCl$_3$): δ 7.73 (d, 1H, J=7.7 Hz), 7.57-7.52 (m, 1H), 7.46-7.40 (m, 1H), 7.36 (d, 1H, J=7.4 Hz), 6.68 (s, 1H), 6.66 (s, 1H), 4.51 (broad s, 1H), 3.85 (s, 3H), 3.65-3.30 (overlapping m, 5H), 3.15-2.98 (m, 2H), 2.78-2.68 (m, 1H). LRMS (ES)$^+$: 349.3 (M+H)$^+$.

Example 14

(±)-cis 6-Methoxy-8-(4-methoxy-2-methylphenyl)-2,3,3a,4,5,9b-hexahydro-1H-pyrrolo [3,4-c]quinoline

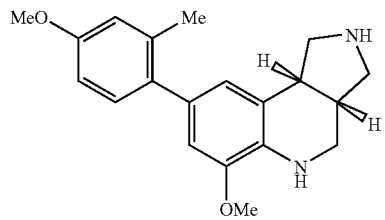

Following the procedures described in Example 12, except that 4-methoxy-2-methylphenylboronic acid was used instead of phenylboronic acid, (±)-cis-tert-butyl 8-bromo-6-methoxy-3,3a,4,5-tetrahydro-1H-pyrrolo[3,4-c]quinoline-2 (9bH)-carboxylate from Example 11, Part A was converted into the title compound of Example 14. $^1$H NMR (CDCl$_3$): δ 7.14 (d, 1H, J=8.1 Hz), 6.83-6.73 (m, 2H), 6.62 (s, 1H), 6.61 (s, 1H), 4.49 (broad s, 1H), 3.85 (s, 3H), 3.84 (s, 3H), 3.78-3.70 (m, 1H), 3.62-3.05 (overlapping m, 6H), 2.83-2.75 (m, 1H), 2.28 (s, 3H). LRMS (ES)$^+$: 325.4 (M+H)$^+$.

Example 15

(±)-cis 8-(2,4-Dichlorophenyl)-6-methoxy-2,3,3a,4,5,9b-hexahydro-1H-pyrrolo[3,4-c]quinoline

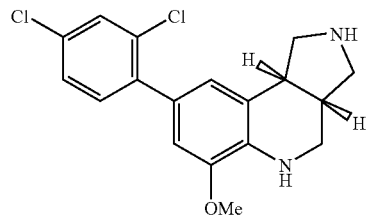

Following the procedures described in Example 12, except that 2,4-dichlorophenylboronic acid was used instead of phenylboronic acid, (±)-cis-tert-butyl 8-bromo-6-methoxy-3,3a,4,5-tetrahydro-1H-pyrrolo[3,4-c]quinoline-2(9bH)-carboxylate from Example 11, Part A was converted into the title compound of Example 15. $^1$H NMR (CDCl$_3$): δ 7.48 (s, 1H), 7.34-7.25 (m, 2H), 6.76 (s, 1H), 6.74 (s, 1H), 4.55 (broad s, 1H), 3.87 (s, 3H), 3.65-3.57 (m, 1H), 3.50-3.25 (overlapping m, 4H), 3.13-2.97 (m, 2H), 2.75-2.65 (m, 1H). LRMS (ES)$^+$: 349.3/351.3 (M+H)$^+$.

Example 16

(±)-cis 6-Methoxy-5-methyl-2,3,3a,4,5,9b-hexahydro-1H-pyrrolo [3,4-c]quinoline

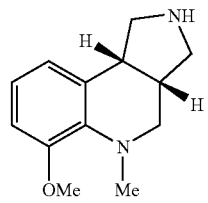

Part A. (±)-cis tert-Butyl 6-methoxy-5-methyl-4-oxo-3,3a,4,5-tetrahydro-1H-pyrrolo [3,4-c]quinoline-2 (9bH)-carboxylate To a suspension of sodium hydride (60 mg of 60% dispersion in mineral oil, hexane-washed, 1.5 mmol) in 5 mL of THF was added (±)-cis tert-butyl 6-methoxy-4-oxo-3,3a,4,5-tetrahydro-1H-pyrrolo[3,4-c]quinoline-2(9bH)-carboxylate from Example 10, Part A (0.40 g, 1.25 mmol) in 4 mL of THF. The reaction was stirred at ambient temperature for 1 h, at which time gas evolution had ceased. Then there was added iodomethane (0.23 mL, 3.75 mmol) and the resulting mixture was allowed to stir at ambient temperature for 18 h. The reaction was quenched with 1N HCl and was extracted with ethyl acetate. The organics were washed with brine, dried (MgSO$_4$) and concentrated in vacuo to afford 0.38 g (91%) of the title compound which was used without purification.

Part B. (±)-cis 6-Methoxy-5-methyl-2,3,3a,4,5,9b-hexahydro-1H-pyrrolo[3,4-c]quinoline Following the procedures described in Example 10, parts B and C, (±)-cis tert-butyl 6-methoxy-5-methyl-4-oxo-3,3a,4,5-tetrahydro-1H-pyrrolo[3,4-c]quinoline-2(9bH)-carboxylate was converted into the title compound of Example 16 as a solid. $^1$H NMR (CDCl$_3$): δ 6.97-6.90 (app t, 1H, J=7.9 Hz), 6.78-6.70 (m, 2H), 4.48 (broad s, 1H), 3.87 (s, 3H), 3.65-3.50 (m, 2H), 3.33-3.23 (m, 1H), 3.08-2.98 (m, 1H), 2.84 (s, 3H), 2.83-2.70 (m, 3H), 2.68-2.58 (m, 1H). LRMS (ESI): 219.3 (M+H)+.

Example 17

(±)-cis 6-Methyl-1,2,3,3a-tetrahydro-5H-pyrrolo[3,4-c]quinolin-4(9bH)-one

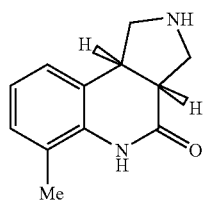

Part A. Diethyl 2-(3-methyl-2-nitrobenzylidene)malonate

To a solution of 3-methyl-2-nitrobenzyl alcohol (16.7 g, 100 mmol) in 300 mL of benzene was added activated manganese (IV) oxide (43.5 g, 500 mmol). The resulting mixture was stirred at 80° C. for 24 h. The reaction mixture was allowed to cool and then was filtered through a pad of Celite and concentrated in vacuo to afford 16.2 g of 3-methyl-2-nitrobenzaldehyde, which was pure enough to be used without purification.

To a solution of this aldehyde (10.0 g, 60.6 mmol) in 20 mL of acetic anhydride was added diethyl malonate (9.7 g, 60.6 mmol) and sodium bicarbonate (7.6 g, 91 mmol). The reaction mixture was stirred at 100° C. for 24 h. The reaction was allowed to cool and then was partitioned between ethyl acetate and water. The organics were washed sequentially with water, aq sat'd NaHCO$_3$ and brine, dried (MgSO$_4$) and concentrated in vacuo. The residue was purified by flash chromatography to afford 16.9 g (90%) of the title compound.

Part B. (±)-cis 6-Methyl-1,2,3,3a-tetrahydro-5H-pyrrolo[3,4-c]quinolin-4(9bH)-one Following the procedures described in Example 9, Parts A-C, diethyl 2-(3-methyl-2-nitrobenzylidene)malonate was converted into the title compound of Example 17 as an off-white solid. $^1$H NMR (CDCl$_3$): δ 7.54 (broad s, 1H), 7.08-7.01 (m, 2H), 6.95-6.87 (m, 1H), 3.66-3.59 (m, 1H), 3.52-3.37 (m, 3H), 3.17-3.07 (m, 1H), 2.83-2.76 (m, 1H), 2.23 (s, 3H). LRMS (ESI): 203.2 (M+H)+.

Example 18

(±)-cis 5,6-Dimethyl-1,2,3,3a-tetrahydro-5H-pyrrolo[3,4-c]quinolin-4(9bH)-one

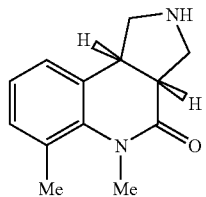

Part A. (±)-cis tert-Butyl 6-methyl-4-oxo-3,3a,4,5-tetrahydro-1H-pyrrolo[3,4-c]quinoline-2(9bH)-carboxylate To a solution of (±)-cis 6-methyl-1,2,3,3a-tetrahydro-5H-pyrrolo[3,4-c]quinolin-4(9bH)-one from Example 17 (4.7 g, 23 mol) in 40 mL of 3N HCl and 40 mL of 1,4-dioxane (from reaction mixture as described in Example 9, Part C) was added 5N NaOH until the pH of the solution was about 12. Then there was added di-tert-butyl dicarbonate (9.8 g, 46 mmol) and the mixture was allowed to stir at ambient temperature for 18 h. The reaction was extracted with ethyl acetate, washed with water and brine, dried (MgSO$_4$) and concentrated in vacuo to afford the title compound.

Part B. (±)-cis 5,6-Dimethyl-1,2,3,3a-tetrahydro-5H-pyrrolo[3,4-c]quinolin-4(9bH)-one To a solution of (±)-cis tert-butyl 6-methyl-4-oxo-3,3a,4,5-tetrahydro-1H-pyrrolo[3,4-c]quinoline-2(9bH)-carboxylate (0.5 g, 1.66 mmol) in 10 mL of DMF and 5 mL of THF was added sodium hydride (0.2 g, 60% dispersion in mineral oil, 5.0 mmol). The mixture was allowed to stir at ambient temperature for 1 h and then there was added iodomethane (0.25 mL, 4.0 mmol). The reaction was allowed to stir at ambient temperature for 18 h. The reaction mixture was poured into brine and extracted with ethyl acetate. The organics were washed with water and brine, dried (MgSO$_4$) and concentrated in vacuo. The residue was purified by flash chromatography to afford 0.47 g (90%) of (±)-cis tert-butyl 5,6-dimethyl-4-oxo-3,3a,4,5-tetrahydro-1H-pyrrolo[3,4-c]quinoline-2(9bH)-carboxylate.

A portion of this material was deprotected as described in Example 10, Part C to afford the title compound of Example 18 as an off-white solid. $^1$H NMR (CDCl$_3$): δ 7.12-7.05 (m, 2H), 7.02-6.95 (m, 1H), 3.83 (dd, 1H, J=1.8, 11.0 Hz), 3.36 (s, 3H), 3.36-3.29 (m, 2H), 3.86-3.18 (m, 1H), 3.01-2.95 (m, 1H), 2.85-2.77 (m, 1H), 2.37 (s, 3H). LRMS (ESI): 217.2 (M+H)+.

Example 19

(±)-cis 6-Methyl-2,3,3a,4,5,9b-hexahydro-1H-pyrrolo[3,4-c]quinoline

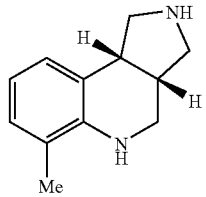

Part A. (±)-cis tert-Butyl 6-methyl-3,3a,4,5-tetrahydro-1H-pyrrolo[3,4-c]quinoline-2(9bH)-carboxylate To a solution of (±)-cis tert-butyl 6-methyl-4-oxo-3,3a,4,5-tetrahydro-1H-pyrrolo[3,4-c]quinoline-2(9bH)-carboxylate from Example 18, Part A (2.4 g, 8 mmol) in 60 mL of THF at 0° C. was added borane THF complex (40 mL of a 1 M solution in THF, 40 mmol) dropwise. The reaction was allowed to warm to ambient temperature and was stirred for 2 h. The reaction was quenched carefully with water and extracted with ethyl acetate. The organics were washed with brine, dried (Na$_2$SO$_4$) and concentrated in vacuo. The residue was purified by flash chromatography to afford 1.55 g (67%) of the title compound. $^1$H NMR (CDCl$_3$) (some signals doubled due to rotamers): δ 6.95-6.90 (m, 1H), 6.65-6.57 (m, 1H), 4.00-2.93 and 3.87-3.80 (m, 1H), 3.66-3.58 (m, 1H), 3.42-2.98 (m, 5H), 2.58-2.44 (m, 1H), 2.11 (s, 3H), 1.44 and 1.43 (s, 9H).

Part B. (±)-cis 6-Methyl-2,3,3a,4,5,9b-hexahydro-1H-pyrrolo[3,4-c]quinoline

Following the procedure described in Example 10, Part C, (±)-cis tert-butyl 6-methyl-3,3a,4,5-tetrahydro-1H-pyrrolo[3,4-c]quinoline-2(9bH)-carboxylate was converted into the title compound of Example 19. $^1$H NMR (CDCl$_3$): δ 6.95-6.87 (m, 2H), 6.65-6.59 (m, 1H), 3.82 (broad s, 1H), 3.68-3.61 (m, 1H), 3.54-3.44 (m, 1H), 3.44-3.37 (m, 1H), 3.30 (dd, 1H, J=4.6, 11.6 Hz), 3.13-2.97 (overlapping m, 3H), 2.70-2.60 (m, 1H), 2.10 (s, 3H). LRMS (ESI): 189.3 (M+H)+.

Example 20

(±)-cis 5,6-Dimethyl-2,3,3a,4,5,9b-hexahydro-1H-pyrrolo[3,4-c]quinoline

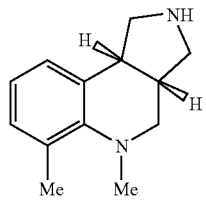

Part A. (±)-cis tert-Butyl 5,6-dimethyl-3,3a,4,5-tetrahydro-1H-pyrrolo[3,4-c]quinoline-2(9bH)-carboxylate To a solution of (±)-cis tert-butyl 5,6-dimethyl-4-oxo-3,3a,4,5-tetrahydro-1H-pyrrolo[3,4-c]quinoline-2(9bH)-carboxylate, an intermediate from Example 18, Part B (0.40 g, 1.27 mmol) in 10 mL of THF at 0° C. was added borane THF complex (6.5 mL of a 1 M solution in THF, 6.5 mmol) dropwise. The reaction was allowed to warm to ambient temperature and was stirred for 2 h. The reaction was quenched carefully with water and extracted with ethyl acetate. The organics were washed with brine, dried (Na$_2$SO$_4$) and concentrated in vacuo. The residue was purified by flash chromatography to afford 0.37 g (97%) of the title compound as an oil.

Part B. (±)-cis 5,6-Dimethyl-2,3,3a,4,5,9b-hexahydro-1H-pyrrolo[3,4-c]quinoline

Following the procedure described in Example 10, Part C, (±)-cis tert-butyl 5,6-dimethyl-3,3a,4,5-tetrahydro-1H-pyrrolo[3,4-c]quinoline-2(9bH)-carboxylate was converted into the title compound of Example 20 as an off-white solid. $^1$H NMR (CDCl$_3$): δ 7.05-6.98 (m, 2H), 6.92-6.85 (m, 1H), 3.58-3.42 (m, 2H), 3.30-3.15 (m, 2H), 3.05-2.97 (m, 1H), 2.75-2.60 (overlapping m, 4H), 2.70 (s, 3H), 2.30 (s, 3H). LRMS (ESI): 203.3 (M+H)+.

Example 21

(±)-cis 8-Bromo-6-methyl-2,3,3a,4,5,9b-hexahydro-1H-pyrrolo[3,4-c]quinoline

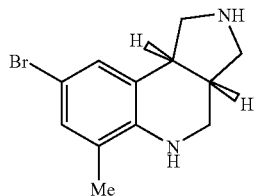

Part A. (±)-cis tert-Butyl 8-bromo-6-methyl-3,3a,4,5-tetrahydro-1H-pyrrolo[3,4-c]quinoline-2(9bH)-carboxylate To a solution of (±)-cis tert-butyl 6-methyl-4-oxo-3,3a,4,5-tetrahydro-1H-pyrrolo[3,4-c]quinoline-2(9bH)-carboxylate from Example 19, Part A (0.87 g, 3.0 mmol) in 15 mL of THF and 4 mL of DMF at −30° C. was added N-bromosuccinimide (0.56 g, 3.15 mmol). The reaction was stirred at −30° C. for 1 h and then was diluted with water and ethyl acetate. The organics were washed with water and brine, dried (Na$_2$SO$_4$) and concentrated in vacuo to afford 0.99 g (90%) of the title compound which was used without purification.

Part B. (±)-cis 8-Bromo-6-methyl-2,3,3a,4,5,9b-hexahydro-1H-pyrrolo[3,4-c]quinoline Following the procedure described in Example 10, Part C, (±)-cis tert-butyl 8-bromo-6-methyl-3,3a,4,5-tetrahydro-1H-pyrrolo[3,4-c]quinoline-2(9bH)-carboxylate was converted into the title compound of Example 21 as a solid. $^1$H NMR (CDCl$_3$): δ 7.04 (s, 1H), 7.01 (s, 1H), 3.84 (broad s, 1H), 3.66 (dd, 1H, J=8.1, 11.4 Hz), 3.51 (dd, 1H, J=7.4, 12.1 Hz), 3.42 (q, 1H, J=8.1 Hz), 3.33-3.26 (m, 1H), 3.14 (dd, 1H, J=4.1, 11.8 Hz), 3.09-2.95 (m, 2H), 2.70-2.60 (m, 1H), 2.07 (s, 3H). LRMS (ESI): 267.2/269.1 (M+H)+.

Example 22

(±)-cis 8-Bromo-5,6-dimethyl-2,3,3a,4,5,9b-hexahydro-1H-pyrrolo[3,4-c]quinoline

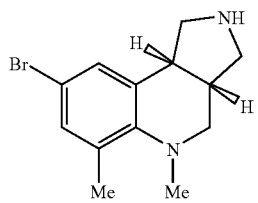

Following the procedures described in Example 21, Parts A and B, (±)-cis tert-butyl 5,6-dimethyl-3,3a,4,5-tetrahydro-1H-pyrrolo[3,4-c]quinoline-2(9bH)-carboxylate from Example 20, Part A, was converted into the title compound of Example 22 as an off-white solid. $^1$H NMR (CDCl$_3$): δ 7.13 (s, 1H), 7.09 (s, 1H), 3.70 (broad s, 1H), 3.61-3.45 (m, 2H), 3.25-3.16 (m, 1H), 3.04-2.98 (m, 1H), 2.80-2.65 (m, 4H), 2.67 (s, 3H), 2.25 (s, 3H). LRMS (ESI): 281.1/283.1 (M+H)+.

Example 23

(±)-cis 6-Methyl-8-phenyl-2,3,3a,4,5,9b-hexahydro-1H-pyrrolo[3,4-c]quinoline

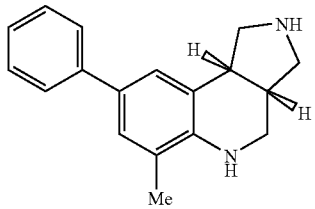

Following the procedures described in Example 12, (±)-cis tert-butyl 8-bromo-6-methyl-3,3a,4,5-tetrahydro-1H-pyrrolo[3,4-c]quinoline-2(9bH)-carboxylate from Example 21, Part A, was converted into the title compound of Example 23 as an off-white solid. $^1$H NMR (CDCl$_3$): δ 7.52-7.43 (m, 2H), 7.41-7.33 (m, 2H), 7.28-7.22 (m, 1H), 7.19 (s, 1H), 7.13 (s, 1H), 3.91 (broad s, 1H), 3.78-3.70 (m, 1H), 3.59-3.48 (m, 2H), 3.38-3.30 (m, 1H), 3.22-3.02 (m, 3H), 2.73-2.62 (m, 1H), 2.15 (s, 3H). LRMS (ESI): 265.3 (M+H)+.

Example 24

(±)-cis 6-Methyl-8-(2-(trifluoromethyl)phenyl)-2,3,3a,4,5,9b-hexahydro-1H-pyrrolo [3,4-c]quinoline

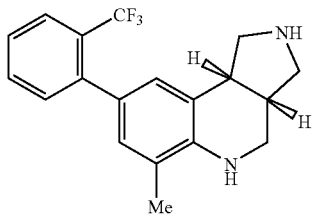

Following the procedures described in Example 13, (±)-cis tert-butyl 8-bromo-6-methyl-3,3a,4,5-tetrahydro-1H-pyrrolo[3,4-c]quinoline-2(9bH)-carboxylate from Example 21, Part A, was converted into the title compound of Example 24 as an off-white solid. $^1$H NMR (CDCl$_3$): δ 7.60 (d, 1H, J=7.3 Hz), 7.45-7.38 (m, 1H), 7.33-7.26 (m, 1H), 7.31-7.25 (m, 1H), 6.86 (s, 1H), 6.79 (s, 1H), 3.80-2.65 (broad overlapping m, 9H), 2.07 (s, 3H). LRMS (ESI): 333.3 (M+H)+.

Example 25

(±)-cis 8-(4-Methoxy-2-methylphenyl)-6-methyl-2,3,3a,4,5,9b-hexahydro-1H-pyrrolo [3,4-c]quinoline

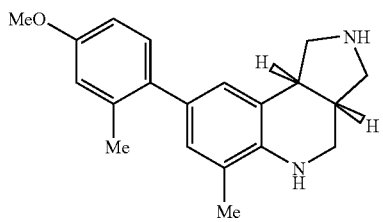

Following the procedures described in Example 14, (±)-cis tert-butyl 8-bromo-6-methyl-3,3a,4,5-tetrahydro-1H-pyrrolo[3,4-c]quinoline-2(9bH)-carboxylate from Example 21, Part A, was converted into the title compound of Example 25 as an off-white solid. $^1$H NMR (CDCl$_3$): δ 7.08 (d, 1H, J=8.6 Hz), 6.88 (d, 1H, J=1.1 Hz), 6.81 (d, 1H, J=1.8 Hz), 6.78-6.70 (m, 2H), 3.87 (broad s, 1H), 3.80 (s, 3H), 3.78-3.73 (m, 1H), 3.62-3.50 (m, 2H), 3.38-3.32 (m, 1H), 3.24 (dd, 1H, J=4.0, 11.7 Hz), 3.18-3.08 (m, 2H), 2.78-2.68 (m, 1H), 2.23 (s, 3H), 2.13 (s, 3H). LRMS (ESI): 309.3 (M+H)+.

Example 26

(±)-cis 8-(2,4-Dichlorophenyl)-6-methyl-2,3,3a,4,5,9b-hexahydro-1H-pyrrolo[3,4-c]quinoline

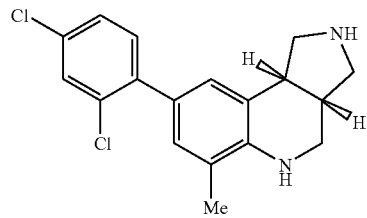

Following the procedures described in Example 15, (±)-cis tert-butyl 8-bromo-6-methyl-3,3a,4,5-tetrahydro-1H-pyrrolo[3,4-c]quinoline-2(9bH)-carboxylate from Example 21, Part A, was converted into the title compound of Example 26 as an off-white solid. $^1$H NMR (CDCl$_3$): δ 7.46 (d, 1H, J=1.8 Hz), 7.30-7.20 (m, 2H), 7.05 (s, 1H), 7.01 (s, 1H), 4.01 (broad s, 1H), 3.80 (s, 3H), 3.78-3.73 (m, 1H), 3.62-3.52 (m, 2H), 3.43-3.37 (m, 1H), 3.26-3.10 (m, 3H), 2.80-2.70 (m, 1H), 2.19 (s, 3H). LRMS (ESI): 333.3/335.3 (M+H)+.

By the procedures described above and by other standard procedures known to those skilled in the art, and using intermediates prepared above, the following compounds of this application were also prepared.

Example 27

(±)-cis 5,6-Dimethyl-N-phenyl-2,3,3a,4,5,9b-hexahydro-1H-pyrrolo[3,4-c]quinolin-8-amine

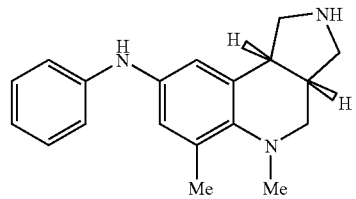

Data for Example 27. $^1$H NMR (CDCl$_3$): δ 7.25-7.17 (m, 2H), 6.95 (d, 2H, J=7.7 Hz), 6.87-6.80 (m, 1H), 6.81 (d, 1H, J=2.2 Hz), 6.72 (d, 1H, J=2.2 Hz), 5.55 (broad s, 1H), 3.90-3.75 (broad m, 2H), 3.58-3.42 (m, 2H), 3.25-3.17 (m, 1H), 3.04-2.97 (m, 1H), 2.78-2.63 (m, 3H), 2.67 (s, 3H), 2.26 (s, 3H). LRMS (ESI): 294.3 (M+H)+.

Example 28

(±)-cis 5,6-Dimethyl-N-(2-(trifluoromethyl)phenyl)-2,3,3a,4,5,9b-hexahydro-1H-pyrrolo [3,4-c]quinolin-8-amine

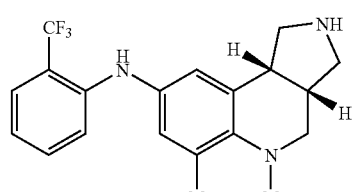

Data for Example 28. $^1$H NMR (CDCl$_3$): δ 7.46 (d, 1H, J=8.1 Hz), 7.30-7.22 (m, 1H), 7.09 (d, 1H, J=8.5 Hz), 6.85-

6.77 (m, 1H), 6.80 (s, 1H), 6.69 (s, 1H), 5.84 (broad s, 1H), 3.70-3.56 (broad m, 2H), 3.43-3.28 (m, 2H), 3.02-2.63 (m, 5H), 2.63 (s, 3H), 2.21 (s, 3H). LRMS (ESI): 362.3 (M+H)+.

Example 29

(±)-cis N-(2,4-Dichlorophenyl)-5,6-dimethyl-2,3,3a,4,5,9b-hexahydro-1H-pyrrolo [3,4-c]quinolin-8-amine

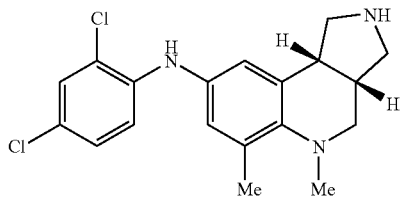

Data for Example 29. $^1$H NMR (CDCl$_3$): δ 7.30 (d, 1H, J=2.2 Hz), 7.06-6.95 (m, 2H), 6.84 (d, 1H, J=2.2 Hz), 6.74 (d, 1H, J=2.2 Hz), 5.86 (broad s, 1H), 3.80-3.50 (m, 4H), 3.38-3.28 (m, 1H), 3.07-3.00 (m, 1H), 2.90-2.70 (m, 3H), 2.69 (s, 3H), 2.27 (s, 3H). LRMS (ESI): 362.3/364.2 (M+H)+.

Example 30

(±)-cis 1-(6-Methoxy-2,3,3a,4-tetrahydro-1H-pyrrolo [3,4-c]quinolin-5(9bH)-yl)ethanone

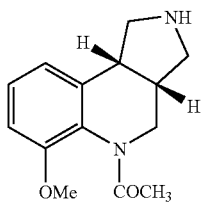

Data for Example 30. $^1$H NMR (CDCl$_3$): δ 7.20-7.10 (m, 1H), 6.90-6.78 (m, 2H), 4.81-4.72 (m, 1H), 3.80 (s, 3H), 3.78-3.65 (m, 2H), 3.20-2.90 (m, 3H), 2.75-2.55 (m, 2H), 1.96 (s, 3H). LRMS (ESI): 247.3 (M+H)+.

Example 31

(±)-cis Methyl 6-methoxy-2,3,3a,4-tetrahydro-1H-pyrrolo[3,4-c]quinoline-5(9bH)-carboxylate

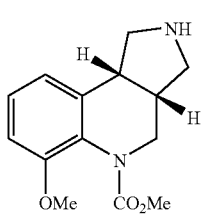

Data for Example 31. $^1$H NMR (CDCl$_3$): δ 7.15 (t, 1H, J=7.9 Hz), 6.85-6.77 (m, 2H), 3.85 (s, 3H), 3.75 (s, 3H), 3.62-3.35 (m, 4H), 3.15-3.03 (m, 2H), 2.90-2.77 (m, 2H). LRMS (ESI): 263.4 (M+H)+.

Example 32

(±)-cis 6-Methoxy-2,3,3a,4-tetrahydro-1H-pyrrolo[3,4-c]quinolin-5(9bH)-yl)(phenyl)methanone

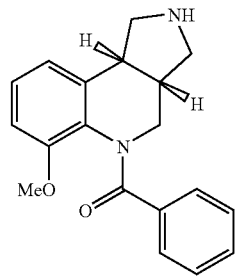

Data for Example 32. LRMS (ESI): 309.3 (M+H)+.

Example 33

(±)-cis N-Benzyl-5,6-dimethyl-2,3,3a,4,5,9b-hexahydro-1H-pyrrolo[3,4-c]quinolin-8-amine

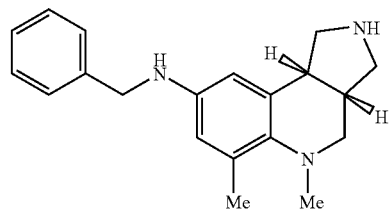

Data for Example 33. $^1$H NMR (CDCl$_3$): δ 7.40-7.25 (m, 5H), 6.40 (d, 1H, J=2.6 Hz), 6.22 (d, 1H, J=2.6 Hz), 4.69 (s, 2H), 4.24 (s, 1H), 3.65-3.56 (m, 1H), 3.36-3.25 (m, 1H), 3.03-2.98 (m, 1H), 2.88-2.64 (m, 5H), 2.61 (s, 3H), 2.22 (s, 3H). LRMS (ESI): 308.3 (M+H)+.

Example 34

(±)-cis N-(2-(Trifluoromethyl)benzyl)-5,6-dimethyl-2,3,3a,4,5,9b-hexahydro-1H-pyrrolo [3,4-c]quinolin-8-amine

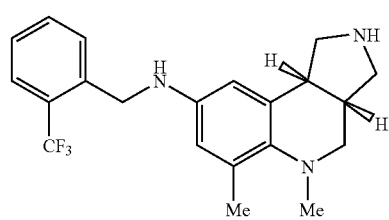

Data for Example 34. LRMS (ESI): 376.3 (M+H)+.

Example 35

(±)-cis N-(2,4-Dichlorobenzyl)-5,6-dimethyl-2,3,3a,4,5,9b-hexahydro-1H-pyrrolo [3,4-c]quinolin-8-amine

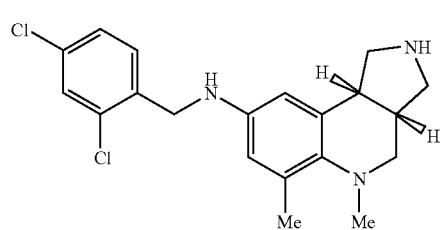

Data for Example 35. $^1$H NMR (CDCl$_3$): δ 7.38 (d, 1H, J=1.9 Hz), 7.31 (d, 1H, J=8.1 Hz), 7.17 (dd, 1H, J=2.0, 8.2

Hz), 6.35 (d, 1H, J=2.5 Hz), 6.15 (d, 1H, J=2.5 Hz), 4.30 (s, 2H), 3.90 (broad s, 1H), 3.68-3.58 (m, 2H), 3.40-3.32 (m, 1H), 3.05-2.75 (m, 5H), 2.61 (s, 3H), 2.21 (s, 3H). LRMS (ESI): 376.3/378.3 (M+H)+.

Example 36

(±)-cis 6-Methoxy-5-methyl-N-phenyl-2,3,3a,4,5,9b-hexahydro-1H-pyrrolo[3,4-c]quinolin-8-amine

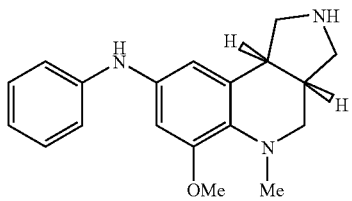

Data for Example 36. $^1$H NMR (CDCl$_3$): δ 7.28-7.19 (m, 2H), 6.98 (d, 2H, J=7.7 Hz), 6.86 (t, 1H, J=7.4 Hz), 6.52 (d, 1H, J=2.2 Hz), 6.46 (d, 1H, J=2.2 Hz), 5.62 (broad s, 1H), 3.81 (s, 3H), 3.72-3.62 (broad m, 1H), 3.60-3.48 (m, 3H), 3.25-3.17 (m, 1H), 3.02 (dd, 1H, J=4.4, 13.6 Hz), 2.82-2.70 (m, 2H), 2.79 (s, 3H), 2.70-2.59 (broad m, 1H). LRMS (ESI): 310.4 (M+H)+.

Example 37

(±)-cis 6-Methoxy-5-methyl-N-(2-(trifluoromethyl)phenyl)-2,3,3a,4,5,9b-hexahydro-1H-pyrrolo[3,4-c]quinolin-8-amine

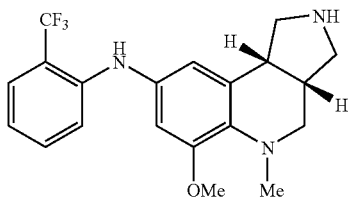

Data for Example 37. $^1$H NMR (CDCl$_3$): δ 7.55 (d, 1H, J=7.7 Hz), 7.36-7.30 (m, 1H), 7.21 (d, 1H, J=8.5 Hz), 6.90 (t, 1H, J=7.5 Hz), 6.57 (s, 2H), 5.97 (s, 1H), 4.84 (broad s, 1H), 3.86 (s, 3H), 3.66-3.56 (m, 3H), 3.32-3.22 (m, 1H), 3.08 (dd, 1H, J=4.2, 13.4 Hz), 2.90-2.80 (m, 2H), 2.85 (s, 3H), 2.73-2.62 (broad m, 1H).

Example 38

(±)-cis N-(2,4-Dichlorophenyl)-6-methoxy-5-methyl-2,3,3a,4,5,9b-hexahydro-1H-pyrrolo [3,4-c]quinolin-8-amine

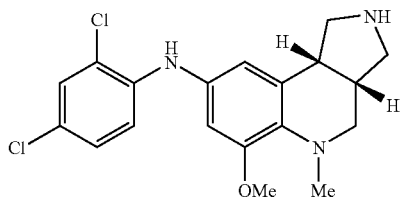

Data for Example 38. $^1$H NMR (CDCl$_3$): δ 7.35 (d, 1H, J=1.8 Hz), 7.11-7.03 (m, 2H), 6.58-6.55 (m, 2H), 5.95 (s, 1H), 3.87 (s, 3H), 3.68-3.56 (m, 3H), 3.33-3.23 (m, 1H), 3.09 (dd, 1H, J=4.4, 13.5 Hz), 2.90-2.80 (m, 2H), 2.86 (s, 3H), 2.74-2.62 (broad m, 1H). LRMS (ESI): 378.2/380.2 (M+H)+.

Example 39

(±)-cis N-(2-(Trifluoromethyl)benzyl)-6-methoxy-5-methyl-2,3,3a,4,5,9b-hexahydro-1H-pyrrolo[3,4-c]quinolin-8-amine

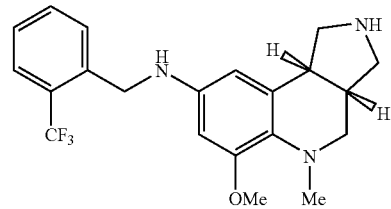

Data for Example 39. $^1$H NMR (CDCl$_3$): δ 7.70 (d, 1H, J=7.6 Hz), 7.63 (d, 1H, J=7.3 Hz), 7.52 (t, 1H, J=7.5 Hz), 7.39 (t, 1H, J=7.7 Hz), 6.07 (s, 1H), 5.98 (s, 1H), 4.51 (s, 2H), 3.84-3.75 (m, 1H), 3.77 (s, 3H), 3.55-3.40 (m, 1H), 3.18-2.50 (broad overlapping m, 6H), 2.79 (s, 3H). LRMS (ESI): 392.2 (M+H)+.

Example 40

(±)-cis N-(2,4-Dichlorobenzyl)-6-methoxy-5-methyl-2,3,3a,4,5,9b-hexahydro-1H-pyrrolo [3,4-c]quinolin-8-amine

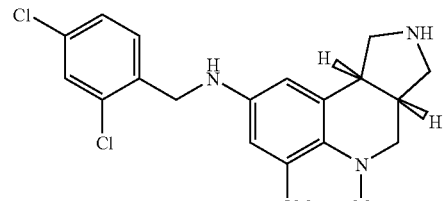

Data for Example 40. $^1$H NMR (CDCl$_3$): δ 7.42 (d, 1H, J=2.2 Hz), 7.37 (d, 1H, J=8.4 Hz), 7.22 (dd, 1H, J=2.2, 8.2 Hz), 6.09 (d, 1H, J=2.2 Hz), 5.96 (d, 1H, J=2.2 Hz), 4.36 (broad s, 2H), 4.09-4.02 (broad m, 1H), 3.82 (s, 3H), 3.72-3.60 (m, 2H), 3.39-3.30 (m, 1H), 3.06 (dd, 1H, J=3.2, 12.7 Hz), 2.98-2.70 (m, 4H), 2.76 (s, 3H). LRMS (ESI): 392.2/394.2 (M+H)+.

Example 41

(±)-cis 2,3,3a,4,5,9b-Hexahydro-1H-pyrrolo[3,4-c]quinoline

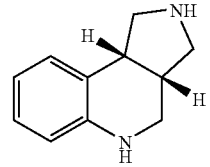

Data for Example 41. $^1$H NMR (CDCl$_3$): δ 7.10-7.00 (m, 2H), 6.73 (td, 1H, J=1.1, 7.3 Hz), 6.61 (d, 1H, J=7.7 Hz), 3.55-3.47 (m, 1H), 3.42-3.30 (m, 1H), 3.30-3.21 (m, 2H), 3.03-2.60 (overlapping m, 5H). LRMS (ESI): 175.2 (M+H)+.

Example 42

(±)-cis 8-(2-(Trifluoromethyl)phenyl)-2,3,3a,4,5,9b-hexahydro-1H-pyrrolo[3,4-c]quinoline

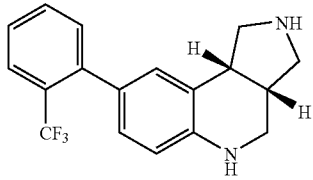

Data for Example 42. $^1$H NMR (CDCl$_3$): δ 7.68 (d, 1H, J=7.7 Hz), 7.53-7.46 (m, 1H), 7.42-7.35 (m, 1H), 7.28 (d, 1H, J=7.7 Hz), 7.00-6.95 (m, 2H), 6.59 (d, 1H, J=8.0 Hz), 4.02 (broad s, 1H), 3.71-3.63 (m, 1H), 3.50-3.03 (overlapping m, 6H), 2.758-2.70 (m, 1H). LRMS (ESI): 319.3 (M+H)+.

Example 43

(4aR,10bR)-1,2,3,4,4a,10b-Hexahydrobenzo[c][2,6]naphthyridin-5(6H)-one

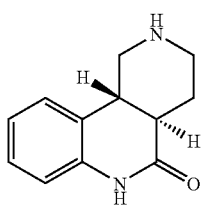

Data for Example 43: LRMS (ESI) 203 (M+H)$^+$.

Example 44

(4aS,10bS)-1,2,3,4,4a,10b-Hexahydrobenzo[c][2,6]naphthyridin-5(6H)-one

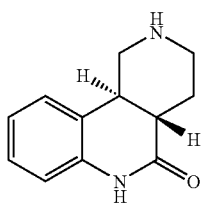

Data for Example 44: LRMS (ESI) 203 (M+H)$^+$.

Example 45

(±)-cis 1,2,3,4,4a,10b-Hexahydrobenzo[c][2,6]naphthyridin-5(6H)-one

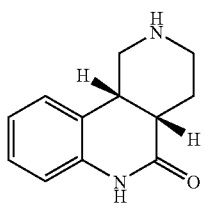

Data for Example 45: LRMS (ESI) 203 (M+H)$^+$.

Example 46

(±)-cis 1,2,3,4,4a,10b-Hexahydrobenzo[c][2,7]naphthyridin-5(6H)-one

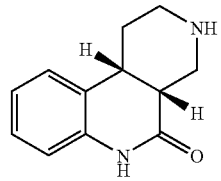

Data for Example 46: LRMS (ESI) 203 (M+H)$^+$.

Example 47

(±)-trans 1,2,3,4,4a,10b-Hexahydrobenzo[c][2,7]naphthyridin-5(6H)-one

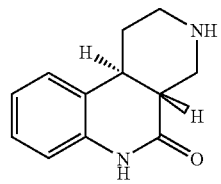

Data for Example 47: LRMS (ESI) 203 (M+H)$^+$.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

A number of references have been cited and the entire disclosures of which are incorporated herein by reference.

What is claimed is:
1. A compound according to Formula I:

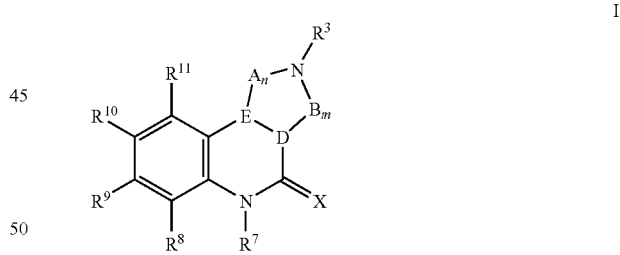

or stereoisomers or pharmaceutically acceptable salt forms thereof, wherein:
A is CR$^1$R$^2$;
B is CR$^4$R$^5$;
D is CR$^6$;
E is CR$^{12}$;
X is selected from the group consisting of O and 2 H;
R$^1$, R$^2$, R$^4$, R$^5$, R$^6$, R$^9$, R$^{11}$ and R$^{12}$ are H;
R$^3$ is independently selected from the group consisting of H, alkyl, alkylaryl and carbooxyalkyl;
R$^7$ is selected from the group consisting of H, alkyl, carboaryl, carboxyaryl and carboxyalkyl,
wherein each alkyl, carboalkyl, carboaryl, carboxyaryl and carboxyalkyl, may optionally be substituted with one or more alkyl, oxyalkyl, halogen, and perfluoroalkyl;

R⁸ is independently selected from the group consisting of H, alkyl, oxyalkyl, halogen and perfluoroalkyl;

R¹⁰ is independently selected from the group consisting of aryl, arylamino, and arylalkylamino, wherein the aryl may be optionally substituted with one or more halogen, alkyl, oxyalkyl, and perfluoroalkyl;

m is 1 or 2; and n is 1 or 2.

2. The compound according to claim 1, wherein: X is O.

3. The compound according to claim 2, wherein: R⁸ is selected from the group consisting of H, alkyl, perfluoroalkyl and halo.

4. The compound according to claim 3, wherein: the perfluoroalkyl is CF₃.

5. The compound according to claim 3, wherein: the halo is chloro.

6. The compound according to claim 3, wherein: the alkyl is methyl.

7. A compound selected from the group consisting of: (±)-cis 6-Methoxy-8-phenyl-2,3,3a,4,5,9b-hexahydro-1H-pyrrolo[3,4-c]quinoline, (±)-cis 6-Methoxy-8-(2-(trifluoromethyl)phenyl)-2,3,3a,4,5,9b-hexahydro-1H-pyrrolo[3,4-c]quinoline, (±)-cis 6-Methoxy-8-(4-methoxy-2-methylphenyl)-2,3,3a,4,5,9b-hexahydro-1H-pyrrolo[3,4-c]quinoline, (±)-cis 8-(2,4-Dichlorophenyl)-6-methoxy-2,3,3a,4,5,9b-hexahydro-1H-pyrrolo[3,4-c]quinoline, (±)-cis 6-Methyl-8-phenyl-2,3,3a,4,5,9b-hexahydro-1H-pyrrolo[3,4-c]quinoline, (±)-cis 6- Methyl -8-(2-(trifluoromethyl)phenyl)-2,3,3a,4,5,9b-hexahydro-1H-pyrrolo[3,4-c]quinoline, (±)-cis 8-(4-Methoxy-2-methylphenyl)-6-methyl-2,3,3a,4,5,9b-hexahydro-1H-pyrrolo[3,4-c]quinoline, (±)-cis 8-(2,4-Dichlorophenyl)-6-methyl-2,3,3a,4,5,9b-hexahydro-1H-pyrrolo[3,4-c]quinoline, (±)-cis 5,6-Dimethyl-N-phenyl-2,3,3a,4,5,9b-hexahydro-1H-pyrrolo[3,4-c]quinolin-8-amine, (±)-cis 5,6-Dimethyl-N-(2-(trifluoromethyl)phenyl)-2,3,3a,4,5,9b-hexahydro-1H- pyrrolo[3,4-c]quinolin-8-amine, (±)-cis N-(2,4-Dichlorophenyl)-5,6-dimethyl-2,3,3a,4,5,9b-hexahydro-1H-pyrrolo[3,4-c]quinolin-8-amine, (±)-cis N-Benzyl-5,6-dimethyl-2,3,3a,4,5,9b-hexahydro-1H-pyrrolo[3,4-c]quinolin-8-amine, (±)-cis N-(2-(Trifluoromethyl)benzyl)-5,6-dimethyl-2,3,3a,4,5,9b-hexahydro-1H-pyrrolo[3,4-c]quinolin-8-amine,(±)-cis N-(2,4-Dichlorobenzyl)-5,6-dimethyl-2,3,3a,4,5,9b-hexahydro-1H-pyrrolo[3,4-c]quinolin-8-amine, (±)-cis 6-Methoxy-5-methyl-N-phenyl-2,3,3a,4,5,9b-hexahydro-1H-pyrrolo[3,4-c]quinolin-8-amine, (±)-cis 6-Methoxy-5-methyl-N-(2-(trifluoromethyl)phenyl)-2,3,3a,4,5,9b-hexahydro-1H-pyrrolo[3,4-c]quinolin-8-amine, (±)-cis N-(2,4-Dichlorophenyl)-6-methoxy-5-methyl-2,3,3a,4,5,9b-hexahydro-1H-pyrrolo[3,4-c]quinolin-8-amine, (±)-cis N-(2-(Trifluoromethyl)benzyl)-6-methoxy-5-methyl-2,3,3a,4,5,9b-hexahydro-1H-pyrrolo[3,4-c]quinolin-8-amine, (±)-cis N-(2,4- Dichlorobenzyl)-6-methoxy-5-methyl-2,3,3a,4,5,9b-hexahydro-1H-pyrrolo[3,4-c]quinolin-8-amine, and (±)-cis 8-(2-(Trifluoromethyl)phenyl)-2,3,3a,4,5,9b-hexahydro-1H-pyrrolo[3,4-c]quinoline.

8. A pharmaceutical composition, comprising: at least one compound according to claim 1; and a pharmaceutically acceptable adjuvant or carrier.

9. A pharmaceutical composition, comprising: at least one compound according to claim 7; and a pharmaceutically acceptable adjuvant or carrier.

* * * * *